(12) United States Patent
Zhang et al.

(10) Patent No.: US 10,590,414 B2
(45) Date of Patent: Mar. 17, 2020

(54) BRUSH POLYMER-ASSISTED COMPACTION OF OLIGONUCLEOTIDES

(71) Applicant: NORTHEASTERN UNIVERSITY, Boston, MA (US)

(72) Inventors: Ke Zhang, Boston, MA (US); Xueguang Lu, Boston, MA (US)

(73) Assignee: NORTHEASTERN UNIVERSITY, Boston, MA (US)

(*) Notice: Subject to any disclaimer, the term of this patent is extended or adjusted under 35 U.S.C. 154(b) by 30 days.

(21) Appl. No.: 15/750,360

(22) PCT Filed: Aug. 4, 2016

(86) PCT No.: PCT/US2016/045576
§ 371 (c)(1),
(2) Date: Feb. 5, 2018

(87) PCT Pub. No.: WO2017/024148
PCT Pub. Date: Feb. 9, 2017

(65) Prior Publication Data
US 2018/0230467 A1 Aug. 16, 2018

Related U.S. Application Data

(60) Provisional application No. 62/202,041, filed on Aug. 6, 2015.

(51) Int. Cl.
C12N 15/113 (2010.01)
A61K 49/00 (2006.01)
C12Q 1/6886 (2018.01)

(52) U.S. Cl.
CPC ........ C12N 15/113 (2013.01); A61K 49/0054 (2013.01); C12N 15/1135 (2013.01); C12Q 1/6886 (2013.01); C08G 2261/1432 (2013.01); C08G 2261/18 (2013.01); C08G 2261/228 (2013.01); C08G 2261/3324 (2013.01); C08G 2261/78 (2013.01); C12N 2310/11 (2013.01); C12N 2310/351 (2013.01);
(Continued)

(58) Field of Classification Search
CPC .............. C12N 15/113; C12N 15/1135; C12N 2310/3515; C12N 2320/32; C12N 2320/11; C12N 2310/51; C12N 2310/351; C12N 2310/11; C12Q 1/6886; A61K 49/0054; C08G 2261/78; C08G 2261/3324; C08G 2261/228; C08G 2261/18; C08G 2261/1432
See application file for complete search history.

(56) References Cited

U.S. PATENT DOCUMENTS 8,968,765 B2* 3/2015 Chen .................. C08G 18/4833
424/426
9,084,825 B2* 7/2015 Montefeltro ....... A61K 31/7105
(Continued)

OTHER PUBLICATIONS

Feuz et al. Langmuir. 2008. 24:7232-7244. (Year: 2008).*
(Continued)

Primary Examiner — Joseph G. Dauner

(57) ABSTRACT

The disclosed subject matter relates to brush polymer-oligonucleotide conjugates comprising oligonucleotides covalently attached to the backbone of a non-cationic, sterically congested brush polymer and the use of such polymer-oligonucleotide conjugates in antisense gene regulation and as diagnostic agents.

18 Claims, 12 Drawing Sheets

Specification includes a Sequence Listing.

(52) U.S. Cl.
CPC .. *C12N 2310/3515* (2013.01); *C12N 2310/51* (2013.01); *C12N 2320/11* (2013.01); *C12N 2320/32* (2013.01)

(56) References Cited

U.S. PATENT DOCUMENTS

| | | | |
|---|---|---|---|
| 9,193,969 B2* | 11/2015 | Montefeltro | A61K 49/0002 |
| 9,867,885 B2* | 1/2018 | Monahan | C08F 293/005 |
| 10,385,335 B2* | 8/2019 | McGall | C40B 50/18 |
| 2002/0001845 A1 | 1/2002 | Klaerner et al. | |
| 2005/0112616 A1* | 5/2005 | Lee | C07H 21/00 |
| | | | 435/6.15 |
| 2005/0164974 A1* | 7/2005 | Gold | A61K 9/1271 |
| | | | 514/44 R |
| 2012/0322991 A1* | 12/2012 | Montefeltro | A61K 49/0002 |
| | | | 536/23.1 |
| 2014/0120158 A1* | 5/2014 | Montefeltro | A61K 31/7105 |
| | | | 424/450 |
| 2014/0315795 A1* | 10/2014 | Carmona Orozco | |
| | | | A61K 31/165 |
| | | | 514/4.8 |
| 2015/0011611 A1* | 1/2015 | Kim | A61K 45/06 |
| | | | 514/44 A |
| 2015/0056158 A1* | 2/2015 | Gunatillake | C08G 83/006 |
| | | | 424/78.29 |

OTHER PUBLICATIONS

Kano et al. Advanced Materials Research. 2008. 47-50: 762-764. Abstract. (Year: 2008).*

Sato et al. Journal of Controlled Release. 2007. 122:209-216. (Year: 2007).*

Jia. "Improving the biopharmaceutical properties of oligonucleotides and oligopeptides through polymer conjugation and architecture design". Dissertion. Jul. 7, 2017. (Year: 2017).*

Lu. "Brush polymers for nucleic acid delivery and self assembly". Dissertation. Apr. 13, 2017. (Year: 2017).*

Lu et al. J Am Chem Soc. 2016. 138:9097-9100. (Year: 2016).*

Shi et al. Biomacromolecules. 2013. 14:1961-1970. (Year: 2013).*

Lu et al. J Am Chem Soc. 2014. 136:10214-10217. (Year: 2014).*

International Search Report and Written Opinion for International Application No. PCT/US2016/45576 dated Dec. 15, 2016; 12 pages.

Gaziova et al. "Chemically Defined Polyethylene Glycol siRNA Conjugates with Enhanced Gene Silencing Effect", Bioorganic & Medicinal Chemistry 22 (2014), 2320-2326.

Lu et al. "Providing Oligonucleotides with Steric Selectivity by Brush-Polymer-Assisted Compaction", J. Am. Chem. Soc. 137 (2015), 12466-12469.

Winkler, Johannes "Oligonucleotides Conjugates for Therapeutic Applications", Ther Deilv. 4(7) (2013), 791-809.

* cited by examiner

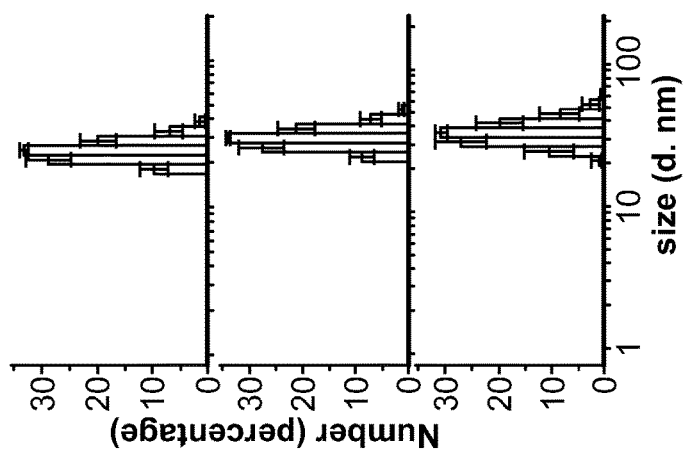
FIG. 2B
FIG. 2C
FIG. 2D
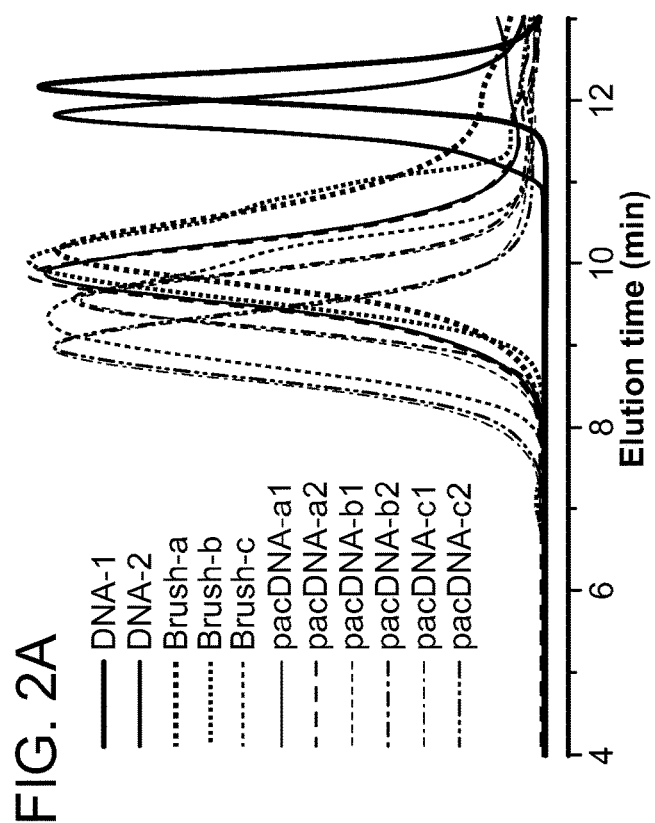
FIG. 2A
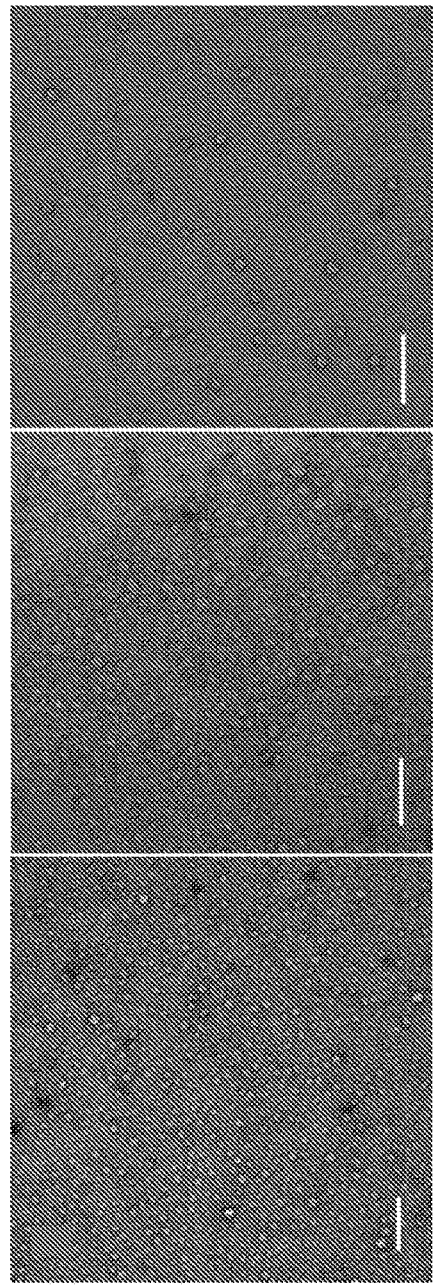
FIG. 2E
FIG. 2F
FIG. 2G

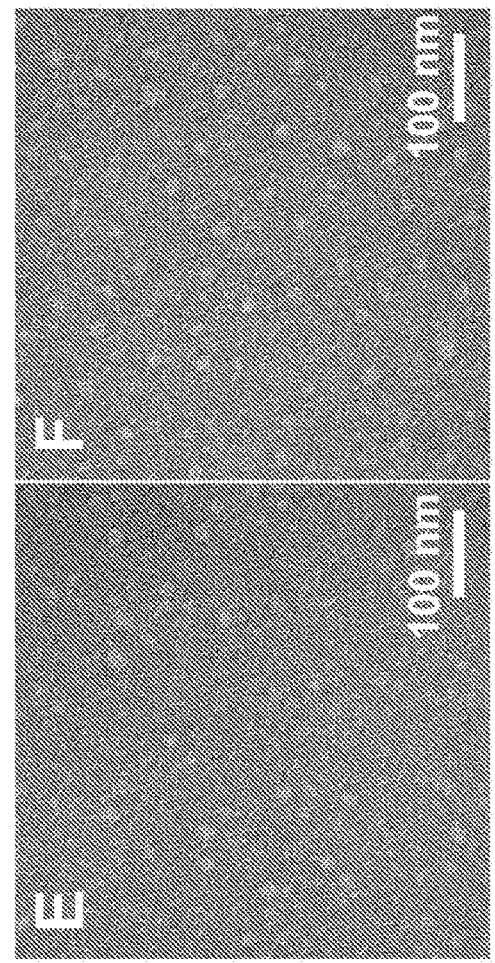
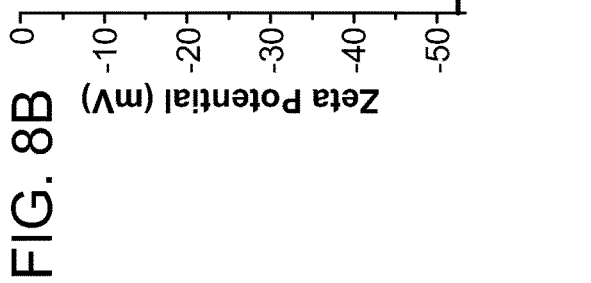
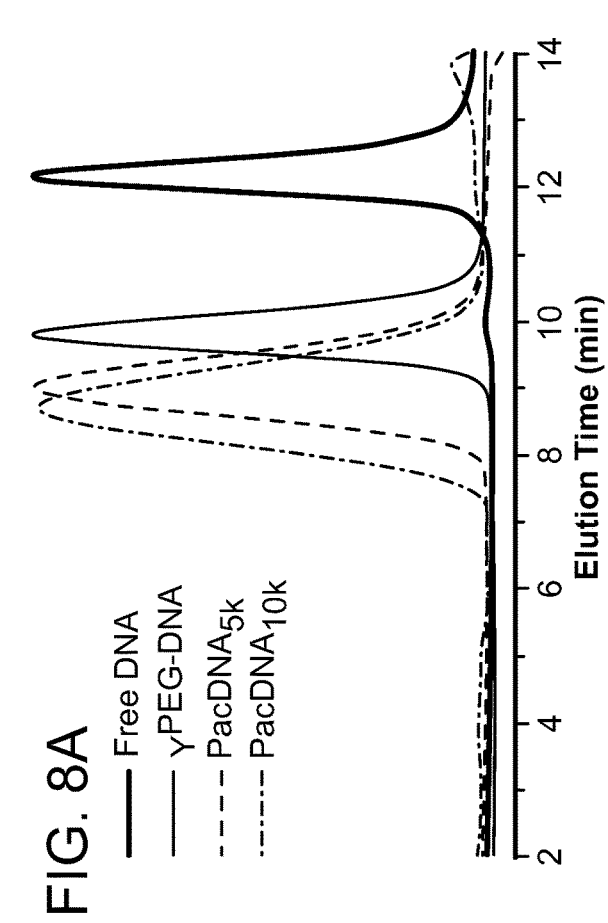
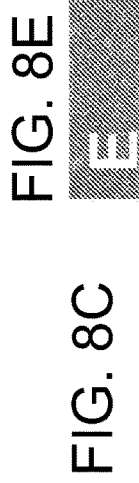
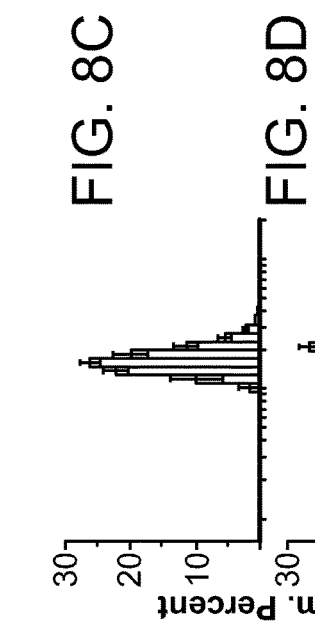

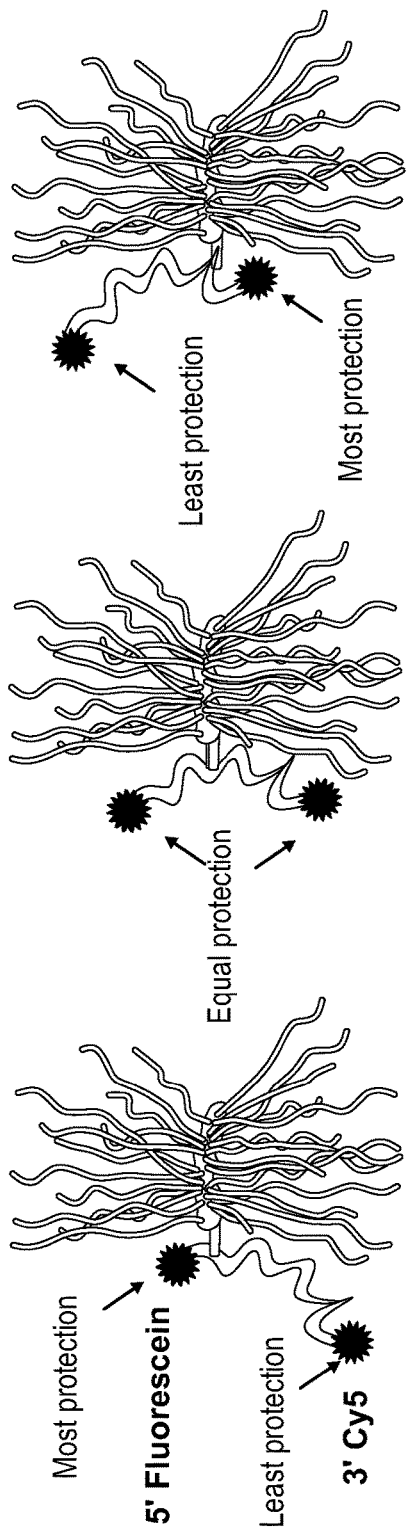
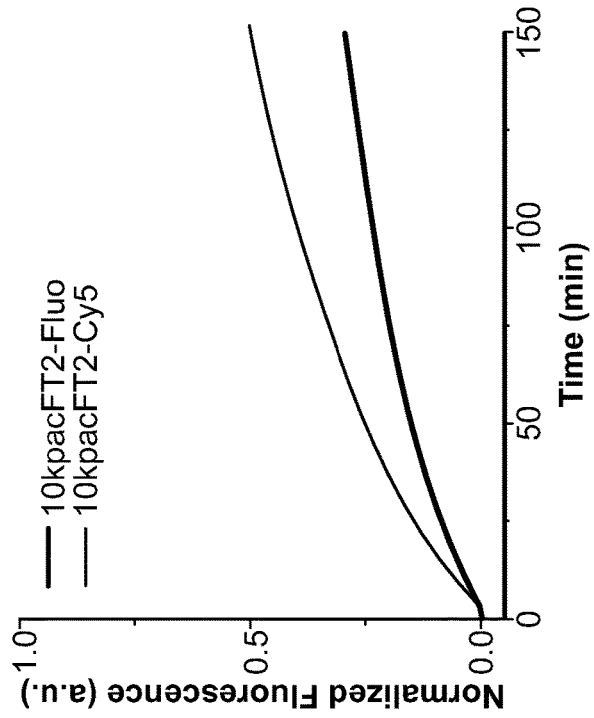
FIG. 14A
FIG. 14B
FIG. 14C

BRUSH POLYMER-ASSISTED COMPACTION OF OLIGONUCLEOTIDES

CROSS REFERENCE TO RELATED APPLICATIONS

This application is a 371 US National Stage of PCT Application No. PCT/US2016/045576, filed on Aug. 4, 2016, which claims the benefit of priority under 35 U.S.C. § 119 to U.S. Provisional Patent Application No. 62/202,041 by Zhang and Lu, filed Aug. 6, 2015, the entire disclosure of which is incorporated herein by reference thereto.

GOVERNMENT FUNDING

This invention was made with government support under Grant No. 1453255 awarded by the National Science Foundation. The government has certain rights in the invention.

SEQUENCE LISTING

The instant application contains a Sequence Listing which has been filed electronically in ASCII format and is hereby incorporated by reference in its entirety. Said ASCII copy, created on Aug. 4, 2016, is named 8190NEU0003PC_SL.txt and is 5,792 bytes in size.

FIELD OF THE INVENTION

This application relates to brush polymer-oligonucleotide conjugates comprising oligonucleotides, covalently attached to the backbone of a non-cationic, sterically congested brush polymer and the use of such polymer-oligonucleotide conjugates in antisense gene regulation and as diagnostic agents.

BACKGROUND

Oligonucleotide-based gene therapy holds tremendous promise for treating a variety of disorders with a genetic basis, including cancers, neurological diseases, and metabolic conditions. However, since its conceptualization in the 1970s, there have only been a relatively small number of commercial successes (e.g., Vitravene, Macugen, and Kynamra), despite powerful advancement in the understanding of the underlying biology. This contrast exemplifies the difficulties in transforming nucleic acids to drugs, which include poor accumulation at target sites, unwanted innate and adaptive immune responses, nuclease degradation, coagulopathy, poor cellular uptake, and overall low biochemical efficacy.

The ability of cationic polymers to complex with nucleic acids and peptides and deliver them to cells has been extensively explored as a route to therapeutic intervention. Despite significant progress, however, these materials are still prone to various degrees of cytotoxic and immunogenic reactions, which limit their clinical application. Recently, a new type of nucleic acid nanostructure, termed spherical nucleic acids (SNAs), emerged as a non-cationic, single-entity transfection agent. Consisting of tens to hundreds of oligonucleotide strands densely arranged onto a spherical core, SNAs are capable of entering cells in large quantities despite their negative charge and knocking down target genes without significant cytotoxicity or stimulation of the innate immune system. Due to the dense arrangement, the SNA oligonucleotides are more stable to nuclease degradation than their free, linear counterparts. However, SNAs interact with protein, such as receptors on the liver, resulting in their capture and uptake by the liver, which limits their residence-time in the blood circulation and hence, ability to reach target cells. Thus, there remain outstanding challenges to the use of oligonucleotides as therapeutics and diagnostic agents and there is a need in the art for methods and delivery systems for delivering oligonucleotides to their target within a cell.

SUMMARY OF THE INVENTION

The invention is directed to a novel form of brush polymer-oligonucleotide conjugates, referred to herein as polymer-assisted compaction of oligonucleotides ("pacOligo," wherein the oligonucleotides may be RNA as well as DNA. The term pacOligo is simply used as shorthand and is not intended to limit the type of nucleic acids comprising the oligonucleotides). The brush polymer-oligonucleotide conjugates of the invention address many of the issues associated with the use of oligonucleotides as therapeutics and diagnostic agents.

In one aspect, the invention provides a brush polymer-oligonucleotide conjugate comprising a plurality of oligonucleotides covalently linked to the backbone of a non-cationic, biocompatible brush polymer. In certain embodiments of this aspect, the brush polymer is polyethylene glycol (PEG), a polysaccharide or a zwitterion polymer. In certain embodiments the oligonucleotide is single stranded or double stranded DNA or double stranded RNA. In another embodiment the brush polymer is a PEG brush polymer. In some embodiments, the plurality of oligonucleotides are complementary to a pre-selected target polynucleic acid.

In another aspect, there is provided a composition comprising the brush polymer-oligonucleotide conjugate comprising a plurality of oligonucleotides covalently linked to the backbone of a non-cationic, biocompatible brush polymer; and a pharmaceutically acceptable carrier.

In another aspect, there are provided methods for inhibiting expression of a gene product encoded by a target polynucleotide comprising contacting the target polynucleotide with a brush polymer-oligonucleotide conjugate of the invention. In various embodiments, expression of the gene product is inhibited in vivo and expression of the gene product is inhibited in vitro. In different embodiments, methods are provided wherein the brush polymer-oligonucleotide conjugate comprises a PEG brush polymer. In other embodiments of this aspect, the brush polymer-oligonucleotide conjugate comprises a PEG brush polymer having a plurality of single stranded RNA molecules covalently attached to the polymer backbone. Methods are also provided wherein the oligonucleotide is bound to the brush polymer through a cleavable linkage.

In another aspect, methods are provided for promoting cellular uptake of an oligonucleotide in a subject or biological sample, comprising delivering an oligonucleotide structure to the subject or the biological sample in an effective amount for promoting cellular uptake of the oligonucleotide, wherein the oligonucleotide structure comprises a plurality of oligonucleotides covalently linked to the backbone of a non-cationic, biocompatible brush polymer. In certain embodiments of this aspect, the brush polymer is a PEG polymer. In other embodiments, the plurality of oligonucleotides is complementary to a target nucleotide sequence associated with a disease state or disorder.

Another aspect of the invention provides methods of detecting the presence of a target polynucleotide in a subject or a tissue sample obtained from a subject comprising contacting the target polynucleotide with the brush polymer-oligonucleotide conjugate comprising a plurality of oligonucleotides covalently linked to the backbone of a non-cationic, biocompatible brush polymer. Methods also include those wherein the brush polymer-oligonucleotide conjugate is optionally labeled with a detectable label.

Consistent with the aspects described herein, brush polymer-oligonucleotide conjugates are provided wherein a plurality of identical oligonucleotide sequences and at least one distinct oligonucleotide sequence are covalently bound to the brush polymer backbone. In other embodiments of the aspects described herein, brush polymer-oligonucleotide conjugates are provided wherein a plurality of identical oligonucleotide sequences are covalently bound to the brush polymer backbone. Also consistent with the aspects described herein, the brush polymer-oligonucleotide conjugate comprises at least two oligonucleotides having different sequences. In certain aspects, the different sequences hybridize to different regions on the same target polynucleotide or the different oligonucleotides hybridize to different target polynucleotides.

Brush polymer-oligonucleotides, compositions and methods are also provided wherein the target polynucleotide is a bacterial polynucleotide, viral polynucleotide or fungal polynucleotide. In embodiments of this aspect, the target nucleotide is either DNA or RNA.
Brush polymer-oligonucleotides, compositions and methods include those wherein expression of the targeted gene product is associated with a disease state. In certain embodiments of this aspect, the disease state is cancer.

In some embodiments of each of the aspects described herein, the brush polymer is a PEG brush polymer.

DESCRIPTION OF THE DRAWINGS

FIG. 2A-G: (A) GPC chromatograms for pacOligos and their macromolecular building blocks. (B-D) DLS number average size distributions for pacOligos a1, b1, and c1. (E-G) TEM images for corresponding pacOligos (negatively stained by uranyl acetate; scale bar is 200 nm.

FIGS. 8A-F: (A) Aqueous GPC chromatograms and (B) zeta potential measurements of free DNA, γPEG-DNA, pacOligo$_{5k}$ (C) and pacOligo$_{10k}$ (D), and corresponding TEM images (E-F) images are negatively stained with uranyl acetate.

FIG. 14A-C: (A) Schematic of different pacOligos in which the oligonucleotide is attached at different positions within the nucleotide sequence to the polymer brush backbone. (B and C): Graphs showing protection of oligonucleotides FT1 (14B) and FT2 (14C) against nuclease degradation.

DETAILED DESCRIPTION OF THE INVENTION

Figure 1:
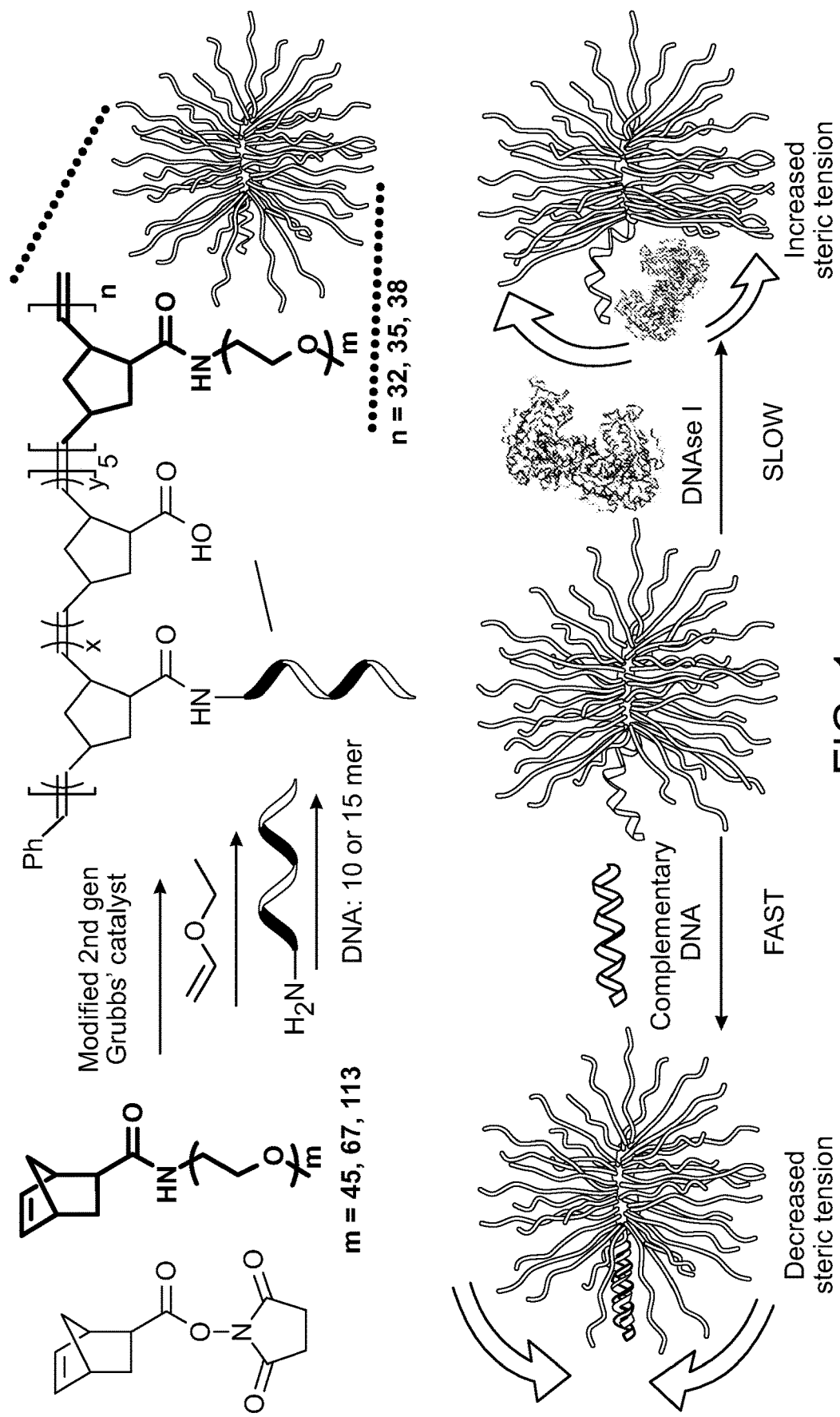
FIG. 1 shows schematics for pacOligo synthesis and mechanism for pacOligo steric selectivity.

The present invention addresses many of the issues associated with use of oligonucleotides as therapeutic agents and diagnostics. It is demonstrated herein that the covalent coupling of one or more oligonucleotides to the backbone of a biocompatible, non-cationic block brush polymer results in protective shielding of the attached oligonucleotides and enables the pacOligo to bypass opsonization. The term "oligonucleotides" as used herein includes modified forms as discussed herein as well as those otherwise known in the art which are used to regulate gene expression.

The inventors have developed a novel form of brush polymer-oligonucleotide conjugates that contain a plurality of oligonucleotides covalently attached to the backbone of a sterically congested brush polymer with polymer side chains. By designing the relative lengths of the oligonucleotide strands and the brush polymer side chains and density of the polymer side chains, the resulting pacOligos can achieve >20-fold increase in half-life of the oligonucleotides for DNase I, while hybridization with complementary strands remains kinetically unaffected. Moreover, the pacOligo can endure the endosome/lysosome environment, and thus enter the cytosol through normal endosomal processing pathways and regulate gene expression with minimal perturbation to the cell.

In contrast, cationic species often cause cell membrane/endosome perforation, leading to toxicity. The use of PEG or other non-cationic, biocompatible polymers for oligonucleotide delivery also improves the biopharmaceutical properties of the oligonucleotides by suppressing unwanted, non-antisense interactions with various proteins. Furthermore, factors previously recognized as important for co-carrier systems such as nucleic acid dissociation from complex and proton buffering capacity do not apply to the pacOligo, thereby simplifying carrier design.

As used herein, the term "brush polymer" means a polymer having an array of macromolecular polymer chains attached to the polymer backbone in sufficient proximity so that the unperturbed solution dimensions (in a good solvent)

of the chains are altered. Furthermore, this close proximity causes overlap of adjacent chains and thus significantly alters the conformational dimensions of individual polymer chains such that they extend or alter their normal radius of gyration to avoid unfavorable interactions.

Any biocompatible non-cationic polymer that does not interact with protein (e.g., exhibits stealth properties which enable it to avoid recognition by liver receptors and other proteins) can be used to generate the brush polymer component of the pacOligo. (See Laschewsky, A., Polymers, 2014, 6, 1544-1601, incorporated herein). For example, polyethylene glycol (PEG) polymers may be used, as well as polysaccharides such as amylose and zwitterion polymers such as poly(methacryloyl-L-lysine), poly(sulfobetaine methacrylate) and poly(carboxybetaine methacrylate).

The brush polymer component of the pacOligo may be a homopolymer, di-block copolymer, a tri-block copolymer, etc., e.g., where one or more blocks are attached with oligonucleotides and the other block(s) form the sidechains. All of the blocks together form the backbone of the brush polymer. The brush polymer consists of a backbone and side chains. Many side chains are tethered to the backbone in close proximity. The backbone can be a homopolymer or a copolymer (diblock, multiblock, or a random mixture of different monomers). The side chain can also be a homopolymer such as PEG, or a copolymer. The side chain may have a different composition from the backbone. For example, the backbone may be polynorbornene and the side chains may be homopolymeric units of PEG, or a zwitterionic polymer or a polysaccharide. In all cases the polymer is non-cationic and biocompatible. Preferably, the polymer component of the pacOligo is a PEG polymer or another polymer having PEG-like properties, e.g., poly(carboxybetaine methacrylate).

The brush polymer can be made by any suitable method for the particular type of polymer being used. For example, PEG brush polymers may be synthesized via sequential ring opening metathesis polymerization (ROMP) of norbornenyl bromide (N—Br) and norbornenyl PEG (N-PEG, Mn=5 or 10 kDa, PDI<1.05), followed by azide substitution of the bromide. The resulting PEG brush polymer is of a diblock structure, with the first block (ca. less than 10 repeating units, such as 1-9, 1-7 or 1-5 repeating units, for example) serving as a reactive region for nucleic acid conjugation, and the second block (ca. more than 2 repeating units, such as 5-80, 5-70, 5-60, 5-50, 10-80, 10-70, 10-60, 10-50 repeating units) creating the brush architecture and the steric congestion needed to protect the nucleic acid.

The brush polymer structure can also be synthesized by atom transfer radical polymerization (ATPR) (See Neugebauer, D., Zhang, Y., Pakula, T., Sheiko, S. S., and Matyjaszewski, K. "Densely-grafted and double-grafted PEO brushes via ATRPA route to soft elastomers." Macromolecules, 2003, 36(18), 6746-6755) or reversible addition—fragmentation chain-transfer polymerization (RAFT) (See Warren, N. J., and Armes, S. P. Polymerization-induced self-assembly of block copolymer nano-objects via RAFT aqueous dispersion polymerization. J. Am. Chem. Soc., 2014, 136(29), 10174-10185), for example.

The lengths of the brush polymer backbone and side chains have an effect on the ability of the pacOligo to avoid opsonization and escape nucleases. The backbone of the brush polymer should be long enough to accommodate a high density of polymer side chains and enable a plurality of oligonucleotides to bind along the length of the backbone. For example, the brush polymer backbone may contain from 3 to 60 repeating polymeric units (a 3mer to 60 mer). Alternatively, the backbone may be a 5 to 50 mer, 5 to 40 mer, 5 to 30 mer, 5 to 20 mer, 5 to 15 mer, 5 to 10 mer, 10 to 50 mer, 10 to 40 mer, 10 to 30 mer, 10 to 20 mer, or 15 to 50 mer, 15 to 40 mer, 15 to 30 mer, 15 to 20 mer, 20 to 50 mer, 20 to 40 mer, or 20 to 30 mer, for example.

Similarly, the length of the brush polymer side chains is selected to provide sufficient protection of the oligonucleotides that are bound to the brush polymer backbone. The length of the brush polymer sidechains is decreased or increased to accommodate the size of the oligonucleotide component. As a general principal, the longer the oligonucleotide, the longer the length of the brush polymer sidechains. In general, the brush polymer side chains are longer (in their coiled state) than the length of the oligonucleotide component. The length of the oligonucleotide component is measured from the point of its attachment to the brush polymer backbone. That is, if the oligonucleotide is attached to the brush polymer backbone from its 5' or 3' end, the length of the brush polymer side chains should be sufficient to protect the entire length of the oligonucleotide. On the other hand, if the oligonucleotide is attached to the brush polymer backbone from an internal thymidine of the oligonucleotide sequence, then the length of the brush polymer side chains need only be as long as or slightly longer than the longest end of the attached oligonucleotide. For example, if a 40 nucleotide oligonucleotide is attached to the brush polymer backbone via an internal T base located at nucleotide 25, then the brush polymer side chains should be of sufficient length to provide protection for a 25 nucleotide long oligonucleotide.

Another factor that affects the protective properties of the brush polymer is the density of the polymer side chains. The brush polymer side chains should be dense enough to create steric congestion, requiring that the brush polymer has sufficiently high degrees of polymerization along the backbone. Owing to advances in ring-opening metathesis polymerization (ROMP) and bioconjugation chemistries, as well as other brush polymer polymerization methodologies, control over this parameter, as well as the lengths of the backbone and side chains, is easily accomplished. (Lu et al., J. Am. Chem. Soc., 2012, 134, 16337; Zhang et al., J. ACS Macro lets., 2013, 2, 809; Gutekunst et al., J. Am. Chem. Soc., 2015, 137, 8038; Jia et al., Chem. Commun., 2015, 71, 7843).

The oligonucleotide component of the pacOligo can be single stranded or double stranded DNA or double stranded RNA. Oligonucleotides contemplated for attachment to a brush polymer backbone include those which modulate expression of a gene product expressed by a target polynucleotide. Accordingly, antisense oligonucleotides which hybridize to a target polynucleotide and inhibit translation, siRNA oligonucleotides which hybridize to a target polynucleotide and initiate an RNAse activity (for example RNAse H), triple helix forming oligonucleotides which hybridize to double-stranded polynucleotides and inhibit transcription, and ribozymes which hybridize to a target polynucleotide and inhibit translation, are contemplated.

Each brush polymer-oligonucleotide conjugate utilized in the compositions and methods provided has a plurality of oligonucleotides attached to the brush polymer backbone. As a result, each brush polymer-oligonucleotide conjugate has the ability to bind to (hybridize with) a plurality of target polynucleotides having a sufficiently complementary sequence. For example, if a specific mRNA is targeted, a single brush polymer-oligonucleotide conjugate has the ability to hybridize with multiple copies of the same transcript. In one embodiment, methods are provided wherein the pacOligo is functionalized with identical oligonucleotides, i.e., each oligonucleotide has the same length and the same sequence. In other embodiments, the pacOligo is functionalized with two or more oligonucleotides, which are not identical, i.e., at least one of the attached oligonucleotides differs from at least one other attached oligonucleotide in that it has a different length and/or a different sequence or modification. In embodiments wherein different oligonucleotides are attached to the brush polymer, these different oligonucleotides hybridize with the same single target polynucleotide, but at different locations, or hybridize with different target polynucleotides which encode different gene products. Accordingly, in various aspects of the invention, a single functionalized pacOligo may be used to inhibit expression of more than one gene product. Oligonucleotides are thus used to target specific polynucleotides, whether at one or more specific regions in the target polynucleotide, or over the entire length of the target polynucleotide as the need may be to effect a desired level of inhibition of gene expression.

"Hybridize" and "hybridization" mean an interaction between two strands of nucleic acids by hydrogen bonds in accordance with the rules of Watson-Crick DNA complementarity, Hoogstein binding, or other sequence-specific binding known in the art. Hybridization can be performed under different stringency conditions known in the art. Under appropriate stringency conditions, hybridization between the two complementary strands could reach about 60% or above, about 70% or above, about 80% or above, about 90% or above, about 95% or above, about 96% or above, about 97% or above, about 98% or above, or about 99% or above in the reactions. It will be understood by those of skill in the art that the degree of hybridization is less significant in the disclosed technology than a resulting degree of inhibition of gene product expression.

The oligonucleotides are designed with knowledge of the target sequence or sequences. Methods of making oligonucleotides of a predetermined sequence are well-known. See, for example, Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are contemplated for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

Alternatively, oligonucleotides are selected from a library. Preparation of libraries of this type is well known in the art. See, for example, Oligonucleotide libraries: United States Patent Application 20050214782, published Sep. 29, 2005.

In another aspect, methods and compositions are provided wherein the oligonucleotide is bound to the brush polymer backbone in such a way that the oligonucleotide is released from the brush polymer after the pacOligo enters a cell. In general an oligonucleotide can be released from the brush polymer using either chemical methods, photon release (i.e., irradiating cells in which pacOligos have entered using an electromagnetic wavelengths chosen based on the pacOligo size), changes in ionic or acid/base environment or a cleavable bond or use of an acid-labile or redox-labile linker, for example.

In one embodiment of this aspect, the oligonucleotide is attached to the brush polymer backbone via a redox-labile moiety and once the functionalized pacOligo is taken into the cell, the oligonucleotide is released from the polymer backbone. For example, a pacRNA structure can be synthesized to feature a redox-labile linker. Once the pacRNA enters the cells, the disulfide bond may be cleaved by glutathione inside the cells and free dsRNA is released to perform gene regulation functionality. This aspect is particular useful in instances where the intent is to saturate the cell with for example, an siRNA and release from the brush polymer backbone would improve kinetics and resolve potential steric hindrance problems. Preparation and use of RNAi for modulating gene expression is well known in the art.

In general, the oligonucleotide, or modified form thereof, is from about 3 to about 80 nucleotides in length. It is also contemplated that the oligonucleotide is about 3 to about 75 nucleotides in length, about 3 to about 70 nucleotides in length, about 3 to about 65 nucleotides in length, about 3 to about 60 nucleotides in length, about 3 to about 50 nucleotides in length about 3 to about 45 nucleotides in length, about 3 to about 40 nucleotides in length, about 3 to about 35 nucleotides in length, about 3 to about 30 nucleotides in length, about 3 to about 25 nucleotides in length, about 3 to about 20 nucleotides in length, about 3 to about 15 nucleotides in length, about 3 to about 10 nucleotides in length, and all oligonucleotides intermediate in length of the sizes specifically disclosed to the extent that the oligonucleotide is able to achieve the desired result. Accordingly, oligonucleotides of 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79 and 80, nucleotides in length are contemplated.

In still other embodiments, oligonucleotides comprise from about 5 to about 60 nucleotides.

In various aspects, the pacOligos, compositions and their use include use of an oligonucleotide which is 100% complementary to the target polynucleotide, i.e., a perfect match or 100% sequence identity over the entire length of the oligonucleotide, while in other aspects, the oligonucleotide is at least about 95% complementary to the polynucleotide over the length of the oligonucleotide, at least about 90%, at least about 85%, at least about 80%, at least about 75%, at least about 70%, at least about 65%, at least about 60%, at least about 55%, at least about 50%, at least about 45%, at least about 40%, at least about 35%, at least about 30%, at least about 25%, at least about 20% complementary to the polynucleotide over the length of the oligonucleotide to the extent that the oligonucleotide is able to achieve the desired degree of inhibition of a target gene product.

Oligonucleotides contemplated for use in the methods include those bound to the brush polymer backbone through any means. Regardless of the means by which the oligonucleotide is attached to the polymer backbone, attachment in various aspects is effected through a 5' linkage, a 3' linkage, some type of internal linkage, or any combination of these attachments. For example, oligonucleotides or a subset of oligonucleotides in any particular pacOligo can be covalently attached at their 5' end to the brush polymer backbone via an amine. In this case, the oligonucleotide is designed to have a 5' amine group. For example, the pacOligo structure is synthesized by coupling amine-modified DNA to a block brush polymer containing N-hydroxyl succinimide (NHS) groups in an aqueous bicarbonate buffer. Alternatively, cyclooctyne-mediated copper-free click chemistry can be used in place of the amidation reaction, resulting in near-quantitative yields. To achieve the coupling, oligonucleotide strand can be modified with 5' dibenzocyclooctyne (DBCO) group, while the brush polymer bears the azide groups. The brush polymers are synthesized using sequential ring opening metathesis polymerization (ROMP) of norbornenyl bromide (N—Br) and norbornenyl PEG (N-PEG, Mn=5 or 10 kDa, PDI<1.05), followed by azide substitution of the bromid, for example. The resulting brush is of a diblock structure, with the first, oligomeric block serving as a reactive region for oligonucleotide conjugation, and the second, longer block creating the brush architecture and the steric congestion needed to protect the oligonucleotide.

Coupling of a DBCO-modified DNA strand to brush polymers is achieved, for example, by incubation in 2 M NaCl solution at 40° C. for 48 h (3:1 alkyne:azide mol:mol). Use of an elevated salt concentration ensures high oligonucleotide loading by screening the charge between nucleic acid strands.

Similarly, the oligonucleotides or a subset of oligonucleotides in any particular pacOligo can be linked to the polymer backbone at the 3' end of the oligonucleotide.

Alternatively, all or some of the oligonucleotides in a pacOligo can be attached to the polymer backbone via an internal thymidine nucleobase of an oligonucleotide. In this case, solid phase DNA synthesis can be used to incorporate amine or alkyne modification at the 5 position of thymine (T) bases, which can be used to couple to brush polymers from any location of the DNA. The modification site of the T base point into the major groove, and does not interfere with the base from participating in hybridization.

The oligonucleotides can be attached to the polymer backbone at any position along the backbone, such as at either end of the polymer backbone or along the internal portion of the polymer backbone. Brush polymers with different DNA attachment points, DNA strands with varying polymer attachment points, and brush polymers of multiple attachment points embedded randomly throughout the backbone are contemplated. With current polymer synthetic methodology (ring opening metathesis polymerization), multi-block brush polymers are readily synthesized by sequential addition of macromonomers. Each step can be monitored to ensure that the monomer is fully consumed before addition of the next monomer. It is understood that different oligonucleotides can be attached at different locations along the length of the polymer backbone. Preferably, but not necessarily, the oligonucleotides are attached at or near either end of the polymer backbone.

In certain embodiments, a detectable label may incorporated at either end of the oligonucleotide to facilitate tracking and quantification of the pacOligo.

Conjugation of the oligonucleotides to the brush polymer backbones via a 5' linkage, 3' linkage or via an internal thymidine nucleobase as disclosed herein provides pacOligo containing a plurality of oligonucleotides. The amount of conjugated oligonucleotides can be adjusted by manipulating the conditions of the linking chemistry. For example, pacOligo containing 2, 3, 4, 5, 6, 7 or more oligonucleotides, which may be the same or different, can be achieved.

In various aspects of the invention, the target polynucleotide is either eukaryotic, prokaryotic, or viral. In various embodiments, the target polynucleotide is an mRNA encoding a gene product and translation of the gene product is inhibited by the pacOligo, or the target polynucleotide is DNA in a gene encoding a gene product and transcription of the gene product is inhibited. The target polynucleotide may be a DNA that encodes a gene product being inhibited or may be complementary to a coding region for a gene product. In still other embodiments, the target DNA encodes a regulatory element necessary for expression of a gene product. "Regulatory elements" include, but are not limited to enhancers, promoters, silencers, polyadenylation signals, regulatory protein binding elements, regulatory introns, ribosome entry sites, and the like. In still, other embodiments the target polynucleotide is a sequence which is required for endogenous replication.

Target regions within a target DNA include any portion of the target nucleic acid, such as the 5' untranslated region (5'UTR) of a gene, the portion of an mRNA in the 5' direction from the translation initiation codon, including nucleotides between the 5' cap site and the translation initiation codon of an mRNA (or corresponding nucleotides on the gene), and the 3' untranslated region (3'UTR), the portion of an mRNA in the 3' direction from the translation termination codon, including nucleotides between the translation termination codon and 3' end of an mRNA (or corresponding nucleotides on the gene).

In some embodiments of the aspects of the invention, the target nucleic acid is a gene or RNA transcript specific to a cancer cell or which is over-expressed in cancer cells, such as HER2, for example, which is over-expressed in several types of cancer, such as breast cancer, ovarian and stomach cancer.

For prokaryotic target polynucleotides, the polynucleotide is genomic DNA or RNA. For eukaryotic target polynucleotides, the polynucleotide is an animal polynucleotide, a plant polynucleotide or fungal polynucleotide, including yeast polynucleotides. The target polynucleotide is either a genomic DNA or RNA. In certain embodiments, the target polynucleotide is a mitochondrial polynucleotide. For viral target polynucleotides, the polynucleotide is viral genomic RNA or transcribed RNA or viral genomic DNA.

Accordingly, the pacOligos described herein may be used to diagnose, prevent, treat or manage certain diseases or bodily conditions. In some cases, the pacOligo structures are both a therapeutic agent and a diagnostic agent. Therapeutic methods provided herein embrace those which result in essentially any degree of inhibition of expression of a target gene product.

In some embodiments, pacOligos described herein may be used as intracellular diagnostic agents. The ability to deliver nucleic acids intact to the cell cytoplasm provides an opportunity to not only regulate RNA targets, but also to detect them. For instance, in some embodiments, delivery of a pacOligo having 3' and/or 5' detectable markers is used to detect the presence of target RNA. In other embodiments, the pacOligo may be designed with oligonucleotides to detect the presence of intracellular proteins (e.g., aptamers) or small molecules through changes in fluorescence that occur due to target protein or small molecule binding, respectively. The pacOligos described herein may be made to deliver nucleic acid sensors for a broad range of biomolecules that provide a convenient readout of their presence, for example, through increased fluorescence upon target molecule binding.

The inventive pacOligos may be used in "pharmaceutical compositions" or "pharmaceutically acceptable" compositions, which comprise a therapeutically effective amount of one or more of the pacOligos described herein, formulated together with one or more pharmaceutically acceptable carriers, additives, and/or diluents. The pharmaceutical compositions described herein may be useful for diagnosing, preventing, treating or managing a disease or bodily condition such as cancer or bacterial or viral infection, for example. It should be understood that any pacOligo described herein can be used in such pharmaceutical compositions.

Pharmaceutical compositions containing the pacOligos may be specially formulated for administration in solid or liquid form, including those adapted for oral administration, for example, drenches (aqueous or non-aqueous solutions or suspensions), tablets, e.g., those targeted for buccal, sublingual, and systemic absorption, boluses, powders, granules, pastes for application to the tongue; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin, lungs, or oral cavity; intravaginally or intrarectally, for example, as a pessary, cream or foam; sublingually; ocularly; transdermally; or nasally, pulmonary and to other mucosal surfaces.

As used herein, the term "pharmaceutically acceptable" refers to those structures, materials, compositions, and/or dosage forms which are, within the scope of sound medical judgment, suitable for use in contact with the tissues of human beings and animals without excessive toxicity, irritation, allergic response, or other problems or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, or solvent encapsulating material, involved in carrying or transporting the pacOligo from one organ, or portion of the body, to another organ, or portion of the body. Each carrier is "acceptable" in the sense of being compatible with the other ingredients of the formulation and not injurious to the patient when administered in doses sufficient to provide a therapeutically effective amount of the brush polymer-oligonucleotide conjugate. Non-limiting examples of materials that can serve as pharmaceutically-acceptable carriers include sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; and other non-toxic compatible substances employed in pharmaceutical formulations.

The pacOligos and compositions containing pacOligo may be orally administered, parenterally administered, subcutaneously administered, and/or intravenously administered for carrying out the methods of the invention. In certain embodiments, a pacOligo or pharmaceutical composition containing a pacOligo is administered orally. In other embodiments, the pacOligo or pharmaceutical composition containing a pacOligo is administered intravenously or via injection into a target site such as a tumor or muscle. Alternative routes of administration include sublingual, intramuscular, and transdermal administrations.

In some embodiments of the invention, the pacOligo or composition containing pacOligo is applied to a biological sample, such as a blood sample or other tissue obtained from a subject, such as a human or other mammal. In this case, the pacOligo is optionally labelled with one or more detectable labels.

Also provided are kits for inhibiting gene expression of a target polynucleotide. In one embodiment of this aspect, the kit contains at least one type of pacOligo as described herein or a plurality of types of pacOligos providing a plurality of different oligonucleotides as described herein attached to a brush polymer backbone. The oligonucleotides on the first type of pacOligo have one or more sequences complementary (or sufficiently complementary as disclosed herein) to one or more sequences of a first portion of a target polynucleotide. The kit optionally includes one or more additional type of pacOligo which has a sequence complementary to one or more sequences of a second portion of the target polynucleotide or to a second target sequence.

In some embodiments of the kits provided, oligonucleotides include a detectable label or the kit includes a detectable label which can be attached to the oligonucleotides or the brush polymer.

EXAMPLES

Materials and Methods Used in Examples 1 and 2

Phorsphoramidites and supplies for DNA synthesis were purchased from Glen Research Co. A-Amine terminated poly(ethylene glycol) methyl ether (Mn=2, 3, 5 kDa, PDI=1.05) were purchased from JenKem Technology USA. All other materials were purchased from Sigma-Aldrich Co., VWR International LLC., or Fisher Scientific Inc., and used without further purification unless otherwise indicated. DLS data were acquired from a MALVERN Zetasizer Nano-ZSP. MALDI-ToF MS measurements were carried out on a Bruker Microflex LT mass spectrometer (Bruker Daltonics Inc., Mass., USA). UV-Vis data were obtained on a Cary 4000 UV-Vis spectrophotometer (Varian Inc., Calif., USA). Fluorescence spectroscopy was performed on a Cary Eclipse fluorescence spectrophotometer. 1H and 13C NMR spectra were recorded on a Varian 400 MHz spectrometer (Varian Inc., Calif., USA). Chemical shifts (j) were reported in ppm. Infrared (IR) spectra were obtained on a Bruker Tensor FT-IR spectrometer (Bruker Corporation). N, N-Dimethylformamide (DMF) GPC was carried out on a TOSOH EcoSEC HLC-8320 GPC system equipped with a TSKGel GMHHR-H, 7.8×300 mm column and RI/UV-Vis detectors. HPLC-grade DMF with 0.2 M LiBr was used as the mobile phase, and samples were run at a flow rate of 0.5 mL/min. GPC calibration was based on polystyrene standards (706 kDa, 96.4 kDa, 5970 Da, 500 Da). Aqueous GPC measurements were performed on a Waters Breeze 2 GPC system equipped with an Ultrahydrogel™ 500, 7.8×300 mm column and a 2998 PDA detector (Waters Co., Mass., USA). Sodium nitrate solution (0.1 M) was used as the eluent running at a flow rate of 0.8 mL/min. Reversephase HPLC was performed using a Waters Breeze 2 HPLC system coupled to a Symmetry® C18 3.5 $_{3m}$, 4.6×75 mm reverse phase column and a 2998 PDA detector, using TEAA buffer (0.1 M) and HPLC-grade acetonitrile as mobile phases. For TEM analysis, samples were deposited on carbon-coated copper grids for 5 min before being carefully wicked away by filter paper. The grids were then stained by pipetting 10 $_3$L of 1.5% uranyl acetate directly onto the grid. The stain was allowed to stay for 3 min before being wicked away. All TEM samples were imaged on a JEOL JEM 1010 electron microscope utilizing an accelerating voltage of 80 kV.

Oligonucleotide Synthesis

Oligonucleotides were synthesized on a Model 391 DNA synthesizer (Applied Biosystems, Inc., Foster City, Calif.) using standard solid-phase phosphoramidite methodology.

Oligonucleotides were purified by reverse-phase HPLC liquid chromatography. All DNA strands were cleaved from the CPG support using aqueous ammonium hydroxide (28-30% NH3 basis) at 55° C. for 17 h. The dimethoxytrityl (DMT) protecting group was removed by treatment with 20% acetic acid in $H_2O$ for 1 h, followed by extraction with ethyl acetate for three times. The successful syntheses of DNA sequences were verified by MALDI-ToF MS.

General Method For Synthesizing Brush Copolymers

Norbornenyl hydroxysuccinimidyl ester (N-NHS) and norbornenyl PEG (N-PEG) were synthesized according to a previously reported method. Modified 2nd generation Grubbs' catalyst was synthesized based on a published protocol. The catalyst (0.02 M) was dissolved in DCM in a 5 mL Schlenk flask. All the monomers (0.04 M) were dissolved in DCM in two different 5 mL Schlenk flasks. All reagents were separately degassed by 3× freeze-pump-thaw cycles. The flask containing N-NHS (5 equiv.) was cooled to −20° C. by using ice-salt bath, to which a solution containing modified Grubbs' catalyst (1 equiv.) was added via a microsyringe. The reaction mixture was stirred for 30 min (TLC shows complete consumption of the N-NHS), before the second monomer, N-PEG (40 equiv.), was added. The reaction mixture was further stirred for 2 h. At the end of the reaction, several drops of ethyl vinyl ether (EVE) were added to the mixture and the reaction was stirred overnight. The mixture was then concentrated and precipitated into ethyl ether 3× and the precipitant was dried in vacuo.

Quantitation of the Available NHS Groups in Brush Polymers

In a round bottom flask, a brush polymer (67 nmol) was dissolved in 2 mL DMF, to which fluorescein 5-thiosemicarbazide (1.43 mg, 3.4 μmol) and DIPEA (0.44 mg, 3.4 μmol) were added. The reaction mixture was allowed to stir at room temperature overnight, before being dialyzed against NaCl solution (0.15 M) using dialysis tubing (MWCO 6-8 kDa) for 48 h. The concentration of fluorescein in the polymer solution was determined by UV-Vis spectroscopy of the brush polymer solution and comparison with a standard curve. The number of fluorescein molecules per polymer was calculated based on the known polymer concentration. Approximately 2.1, 2.0, and 2.4 fluorescein tags were attached to brushes a-c, respectively.

General Method for Synthesizing PacOligo

Brush polymers were dissolved in anhydrous DMSO (ca. 100 μL) to give a final concentration of 1 mM. Amine-modified DNA (15 nmol) was dissolved in 10 μL aqueous buffer containing NaHCO3 (50 mM) and NaCl (1 M). The polymer solution (5 μL) was added to the DNA solution, and the mixture was shaken gently overnight at 0° C. on an Eppendorf Thermomixer. The reaction mixture was then dialyzed against Nanopure™ water using a MINI dialysis unit (MWCO 3500 Thermo Fisher) for desalting. The dialysate was further subjected to aqueous GPC purification. The fraction containing the conjugate was collected and dialyzed against Nanopure™ water to remove NaNO3. The final solution was lyophilized to yield a light-green powder.

Polymer Weight Percent of PacOligo

For determining the size of the pacOligo, the shape of the brush polymer-oligonucleotide conjugate is assumed to be spherical. The exclusion volume of the brush polymer-oligonucleotide conjugates, e.g., PEG-DNA can be determined by measuring diameter via dynamic light scattering (DLS) and data are listed in Table below for PEG-DNA conjugates. Free DNA and 2 kDa PEG-DNA could not be measured by DLS due to the poor correlation function. Weight percent of PEG (mg/1004) can then be estimated.

The results indicate that the structure of pacOligo can provide more exclusion volume to the oligonucleotide strand. This modification approach can introduce localized crowding effect and then influence properties of oligonucleotide.

TABLE A

Diameter and PEG weight percent of PEG-DNA conjugates.

| Item | Diameter (nm) | Standard Deviation (nm) | PEG weight percent |
|---|---|---|---|
| 5 kDa PEG-DNA | 5.501 | 1.983 | 9.53 ± 4.61 |
| 40 kDa PEG-DNA | 10.19 | 2.775 | 12.00 ± 4.38 |
| 40 kDa YPEG-DNA | 10.5 | 2.588 | 10.97 ± 3.62 |
| 5k pacOligo | 15.75 | 4.206 | 15.44 ± 5.64 |
| 10k pacOligo | 16.93 | 4.614 | 16.00 ± 5.73 |

Hybridization Kinetics Assay

All free DNA and pacOligo were each dissolved in microcentrifuge tubes in PBS buffer (pH=7.4) to give a final concentrations of 100 nM. Each solution (1 mL) was transferred to a fluorescence cuvette, to which a complementary dabcyl-DNA strand or a dummy DNA strand (2 equiv.) was added via 1 μL of PBS solution and thoroughly mixed. The fluorescence of the mixture (ex=490 nm, em=520 nm) was monitored before the mixing every 3 sec using a Cary Eclipse fluorescence spectrometer, and the monitoring was continued for 60 min after the mixing. The endpoint is determined by adding a large excess of complementary dabcyl-DNA to the mixture followed by incubation for an extended period of time (>1 h). The kinetics plots are normalized to the end points determined for each sample.

Nuclease Degradation Kinetics Assay

All free DNA and pacOligo (1 μM) were each mixed with their respective complementary dabcyl-labeled DNA (2 μM) in PBS buffer. The mixtures were heated to 80° C. and allowed to cool slowly to room temperature in a thermally insulated container during a period of 10 h. The mixture was then diluted to 100 nM in assay buffer (10 mM tris, 2.5 mM $MgCl_2$, and 0.5 mM $CaC_2$, pH=7.5), and 1 mL of the mixture was transferred to a fluorescence cuvette which was mounted on a fluorimeter. DNase I (Sigma-Aldrich) was then added and rapidly mixed to give a final concentration of 0.1 unit/mL. The fluorescence of the samples (ex=490 nm, em=520 nm) was measured immediately and every 3 sec for 6 h. The endpoint was determined by adding a large excess of DNase I (ca. 2 units/mL) to the mixture, and the fluorescence was monitored until no additional increase was observed. The kinetics plots were normalized to the endpoints determined for each sample, and all experiments were performed in triplicates.

General Method for the Synthesis of Dual-Labeled PacOligo for In Vivo Imaging

Brush polymers and Cy5.5 hydrazide were dissolved in anhydrous DMSO in separate flasks to give stock solutions with a final concentration of 1 mM. DNA-1' was dissolved in an aqueous buffer containing $NaHCO_3$ (50 mM) and NaCl (1 M) with a concentration of 1 mM. Then, DNA-1' (200 μL), the brush solution (100 μL), and the Cy5.5 solution (20 μL) were rapidly mixed in a microcentrifuge tube and shaken gently at 0° C. overnight on an Eppendorf Thermomixer. For the brush-c polymer control (no DNA), only the polymer and Cy5.5 stock solutions were mixed. The reaction mixture was then dialyzed first against 0.5 M NaCl solution, and then against Nanopure™ water, using MINI dialysis units (MWCO 3500 Da) to remove residue Cy5.5 and DMSO. The aqueous solution was further purified by aqueous GPC. The fraction containing the conjugate was collected and desalted by dialysis. The final solution was lyophilized to yield a purple powder. UV-Vis spectroscopy indicated that there are 0.2 Cy5.5 and 1.8 DNA-1' per brush-c.

Mouse Model and In Vivo Imaging

Nude mice were orthotopically implanted with mouse breast cancer cells (4T1) in the right mammary fat pad. Animals were divided into six groups: pacOligos, brush polymers, free dye, free DNA, with each group having two to three animals. All samples dispersed in PBS buffer were injected intravenously via tail vein on day 21 post-tumor implantation with equivalent dose of Cy5.5. The mice were fed with a special diet 5 days before the imaging study to eliminate any interference of fluorescence from the food. In vivo images were acquired at different time points 1-24 h post-injection in an IVIS instrument (PerkinElmer Inc., USA). The animals were sacrificed at 24 h post-injection and perfused with PBS to remove blood from all organs. Clean organs were used for ex vivo imaging of tissues (Cy3 and Cy5.5 channels).

the brushes. To quantify the number of reactive NHS esters available for coupling, polymers and an excess amount of fluorescein 5-thiosemicarbazide are allowed to react overnight in dimethylformamide (DMF). After removing the unreacted fluorescein by dialysis, optical absorbance was measured and compared to a standard curve to calculate the number of NHS groups per polymer. For brushes a-c, there are 2.1, 2.0 and 2.4 NHS esters, respectively.

TABLE 2

GPC analyses for the brush polymers used.

| Polymer | Composition | PDI | Mn (kDa) | Mw (kDa) |
|---|---|---|---|---|
| Brush-a | pN-NHS$_2$-b-pN-PEG(2k)$_{38}$ | 76.3 | 88.8 | 1.18 |
| Brush-b | pN-NHS$_2$-b-pN-PEG(3k)$_{32}$ | 96.2 | 106.2 | 1.10 |
| Brush-c | pN-NHS$_2$-b-pN-PEG(5k)$_{35}$ | 174.3 | 196.4 | 1.13 |

For conjugation to the brushes, the DNA strands are designed to have a 5' amine group. A fluorescein tag is also incorporated at the 3' to facilitate tracking and quantification. The conjugation is carried out in pH 8.0 bicarbonate

TABLE 1

Oligonucleotide sequences used in Examples 1-3

| Name of Strand | Application | Sequence |
|---|---|---|
| DNA-1 | Couples with p(N-NHS)$_2$-bp(N-PEG)$_n$ | 5'-NH$_2$-CCC AGC CCT C fluorescien-3' (SEQ ID NO.: 1) |
| DNA-2 | Couples with p(N-NHS)$_2$-bp(N-PEG)$_n$ | 5'- NH$_2$-CCC AGC CTT CCA GCT-fluorescien-3' (SEQ ID NO.: 2) |
| DNA-3 | Antisense strand of DNA-1 | 5'-Dabcyl-GAG GGC TGG G-fluorescein-3' (SEQ ID NO.: 3) |
| DNA-4 | Antisense strand of DNA-2 | 5'-Dabcyl-AGC TGG AAG GCT GGG-3' (SEQ ID No.: 4) |
| DNA-5 | Dummy dabcyl DNA | 5'-NH$_2$-TTT ACT-dabcyl AAC CTT TCC GTC GCA GCA AAA-3' (SEQ ID NO.: 5) |
| DNA-1' | Cy3-modified strand for in vivo imaging | 5'-NH$_2$-CCC AGC CCT C-Cy3-3' (SEQ ID NO.: 6) |
| DNA-6 | Cy5.5-modified strand for in vivo imaging | 5'-Cy5.5-CCC AGC CCT C-3' (SEQ ID NO.: 7) |

Example 1

To systematically probe the relationship between the structural parameters of the pacOligo and its steric selectivity, a library of six pacOligo structures has been synthesized by conjugating two DNA strands (10 or 15 bases; DNA-1: 5'-NH$_2$-CCC AGC CCT C-F-3'(SEQ ID NO.: 1) and DNA-2: 5'-NH$_2$-CCC AGC CTT CCA GCT-F-3'(SEQ ID NO.: 2)) with three brush polymers (brushes a-c: side chain PEG Mn=2, 3, 5 kDa, respectively; PDI<1.05). The brushes are synthesized via sequential ROMP of norbornenyl hydroxysuccinimidyl ester (N-NHS) and norbornenyl PEG (N-PEG), to yield a diblock architecture (pN-NHS$_{2-3}$-b-pN-PEG$_{32-38}$. (Table 2). The short first block containing NHS esters is incorporated for subsequent coupling with amine-modified DNA strands. Gel permeation chromatography (GPC) shows narrow molecular weight distribution for all brush polymers. Infrared spectroscopy shows characteristic vibrations of the NHS groups at 1739 cm$^{-1}$, 1780 cm$^{-1}$, and 1807 cm$^{-1}$), confirming their successful incorporation into buffer at 0° C. using an excess of DNA, and the products are purified by aqueous GPC equipped with a photodiode array detector. The conjugates have a much larger molecular weight compared with free DNA, and thus the two components have baseline separation. Chromatograms for purified pacOligo show no residue of free DNA (FIG. 1A). Quantification of the amount of DNA strands per brush by peak integration indicates that there are 1-2 strands for each pacOligo (Table 3), which is consistent with the numbers of reactive NHS ester groups. Dynamic light scattering (DLS) shows that pacOligos have number-average hydrodynamic diameters between 25±5 nm and 32±8 nm, with narrow size distributions (PDI<0.1). Transmission electron microscopy (TEM) shows a morphology for all pacOligos with a dry-state diameter in the range of 27±4 to 31±5 nm. The spherical morphology is expected because the brush polymers are structurally analogous to star polymers if one considers the relatively short backbone length. Representative DLS size distributions and TEM images are shown in FIG. 2B-G.

TABLE 3

Number of DNA strands per pacOligo

| pacOligo | a1 | b1 | c1 | a2 | b3 | c3 |
|---|---|---|---|---|---|---|
| #DNA/pacOligo | 2.3 | 1.4 | 1.5 | 1.5 | 1.4 | 1.9 |
| $D_{h(n)}$ (nm) | 25 ± 5 | 30 ± 7 | 32 ± 8 | 25 ± 5 | 33 ± 8 | 34 ± 8 |

To examine whether the brush component inhibits DNA hybridization, a fluorescence quenching assay was used in which a quencher (dabcyl)-linked complementary DNA strand is added to fluorescein-tagged pacOligo. The rate at which fluorescence decreases is an indicator of the kinetics for duplex formation (FIG. 3). All pacOligos are mixed with 2 equiv. of complementary dabcyl-DNA in phosphate buffered saline at room temperature. A dummy strand (DNA-5) that is unable to form a duplex with the pacOligo is used as a control. Fluorescence is measured immediately upon mixing and every 3 sec for 60 min. Strikingly, all pac-DNAs hybridize immediately with their respective antisense dabcyl-DNA strands (FIG. 3B), with little to no difference in the kinetics between the pacOligo and the free DNA. When the dummy dabcyl-DNA control is used in the presence of free DNA or pacOligo, fluorescence signals remain constant, ruling out non-specific binding. Although the slower diffusion of pacOligo should in theory decrease the hybridization kinetics, the DNA strand within a pacOligo is likely pre-oriented by the dense PEG side chains, which facilitates hybridization. The apparent lack of change in the kinetics may be the result of the two effects offsetting each other. There are, however, significant differences in the hybridization kinetics between DNA-1 and DNA-2, and between the pacOligos containing them. This observation is likely because DNA-2 can form a hairpin structure (calc $T_m$=34.1° C.). The intramolecular secondary structure stabilizes single-strand conformation and increases the energy barrier for intermolecular hybridization, which then slows the hybridization kinetics.

Figure 3A:
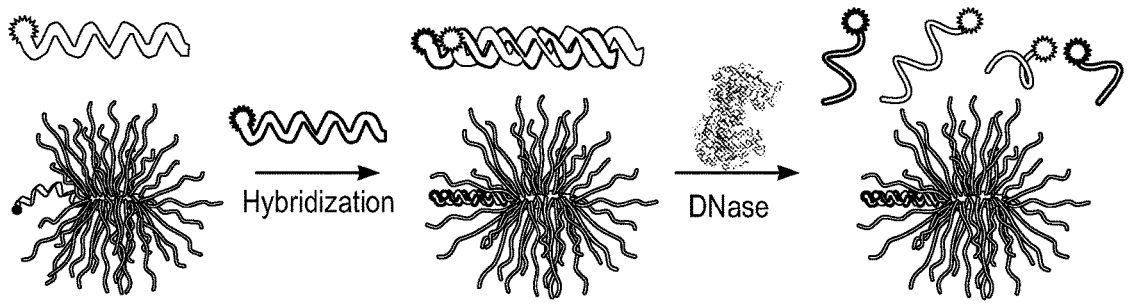
FIGS. 3A-C: (A) Schematics for assays for determining DNA hybridization and nuclease degradation kinetics. (B) Hybridization kinetics for pacOligo versus free DNA. (C) Nuclease activity kinetics for pacOligo versus free DNA.
Figure 3B:
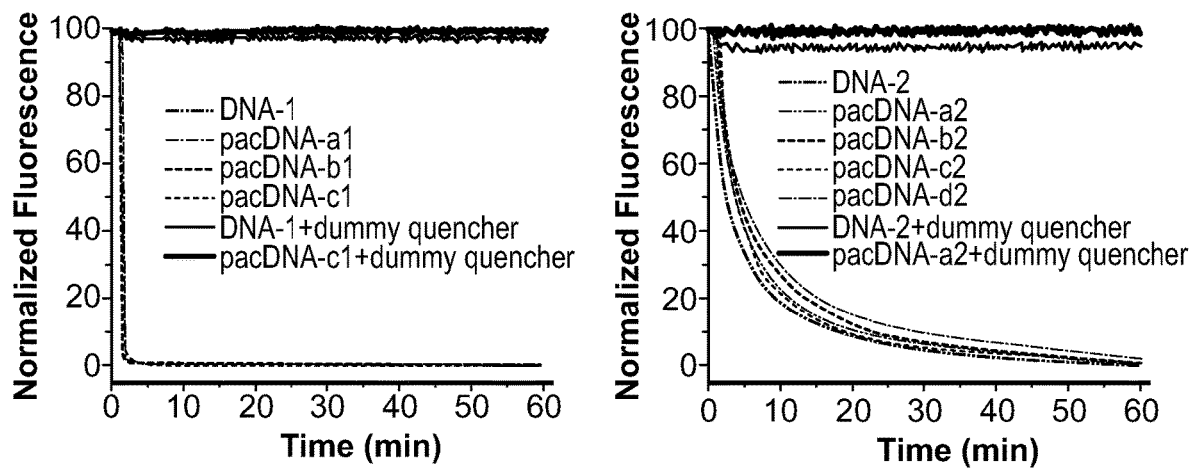
Figure 3C:
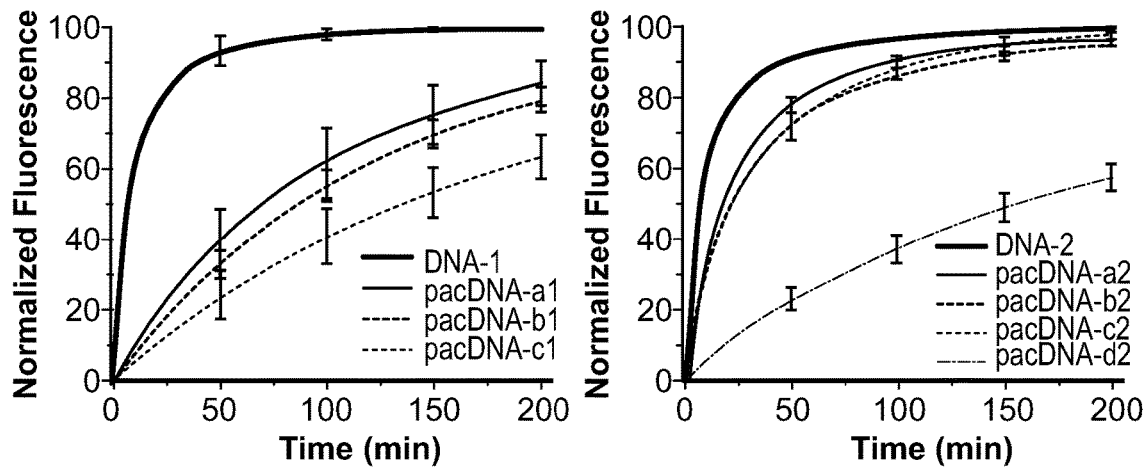

To test whether pacOligos are able to sterically inhibit proteins from accessing their DNA component, DNase I is used as a model protein to act on fluorescein-pacOligos that are pre-hybridized with dabcyl-DNA (FIG. 3A). The fluorescence of the pacOligos are quenched when hybridized. When DNase I is introduced, the duplexes are degraded, and the fluorophores are released, leading to an increase of fluorescence (FIG. 3A). While free DNA-1 and DNA-2 duplexes are both degraded rapidly, with half-lives of 9.3±4.2 min and 7.3±1.7 min, respectively, all pacOligo conjugates show enhanced stability against the enzyme, as evidenced in prolonged half-lives and reduced initial rates (FIG. 3C-E). The best among these is pacOligo-c1, which has the longest PEG side chain (5 kDa) and the shorter DNA component, showing ca. 14.5× longer half-life and ca. 0.09× of the initial enzymatic activity. In contrast, pacOligo-a2, having the shortest PEG side chains (2 kDa) and the longer DNA-2, shows only ca. 2.4× increase in half-life and 0.47× of the initial degradation rate. These results indicate that, provided with appropriate design parameters, the pacOligo can achieve substantial selectivity for DNA hybridization versus protein recognition. On the molecular level, such selectivity is possible for two reasons. First, the DNA is ca. 18-22 angstroms wide, while proteins are generally 3-10 nm in hydrodynamic diameter, giving complementary DNA a kinetic advantage for access. Second, upon hybridization, the dsDNA becomes more stiff compared with the ssDNA and therefore some of the hydrodynamic volume that it occupies can be released, which in turn relaxes the tension caused by the congestion of the side chains of the brush polymer. On the other hand, in order for a protein to access the ssDNA confined within the dense side chains, the tension instead would have to increase. Thus, both kinetics and thermodynamics favor DNA hybridization and disfavor binding with a protein.

Example 2

Figure 4A:
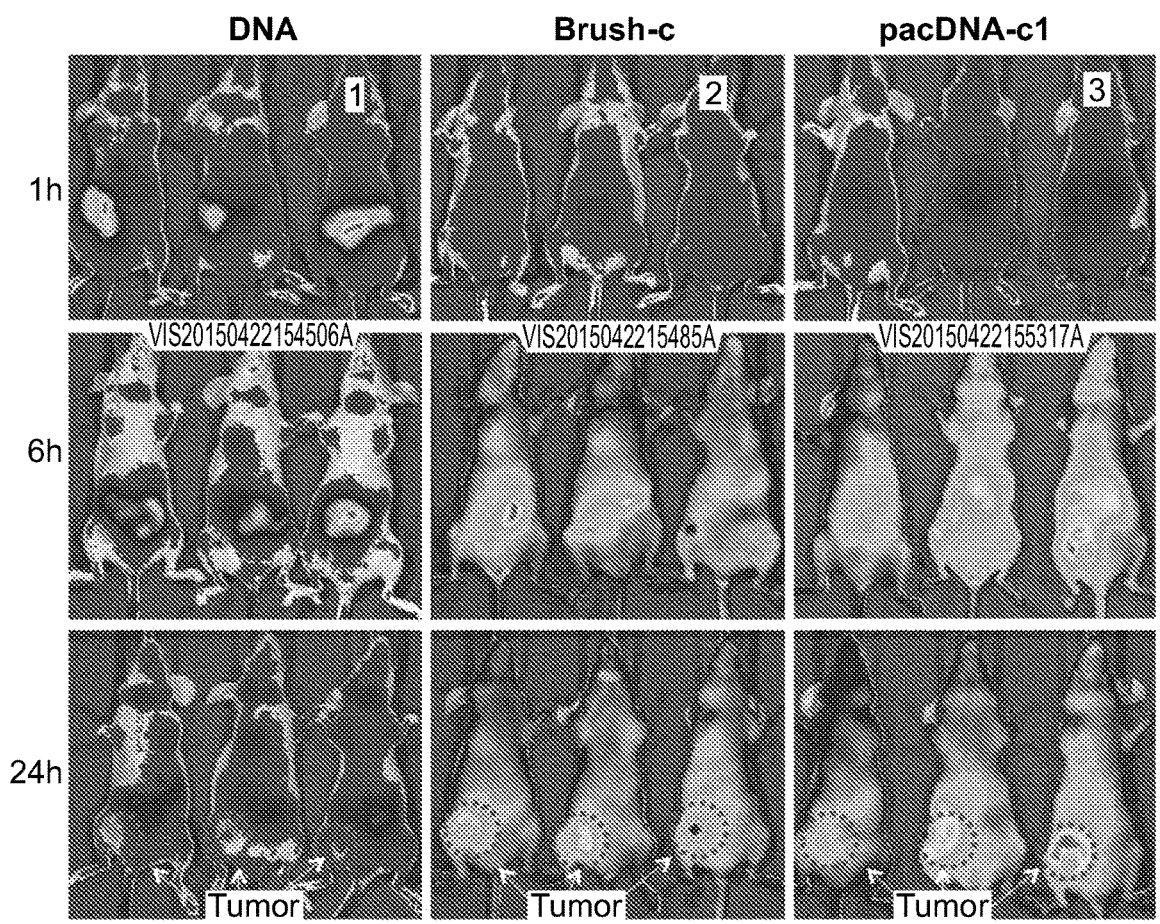
FIG. 4A-C: (A) Near IR-imaging of live mice over 24 h (Cy5.5 channel). (B) Ex vivo imaging of tissues from numbered mice (T-tumor; H-heart; Lg-lung; K-kidney; S-spleen; Lv-liver). (C) Dual-channel imaging of organs from mice treated with dual-labelled pacOligo (polymer: Cy5.5, DNA Cy3).
Figure 4B:
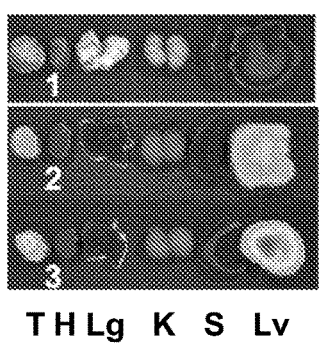
Figure 4C:
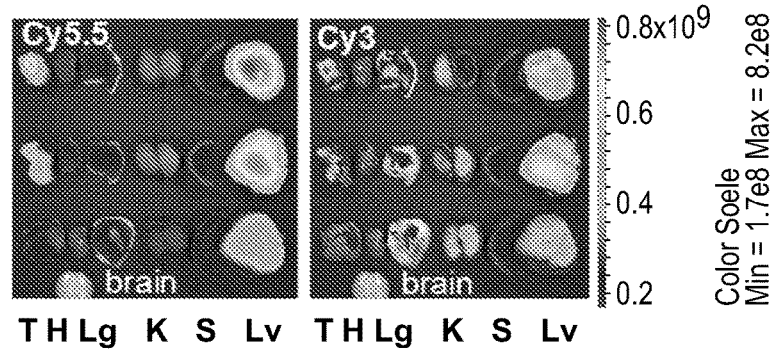
Figure 5A:
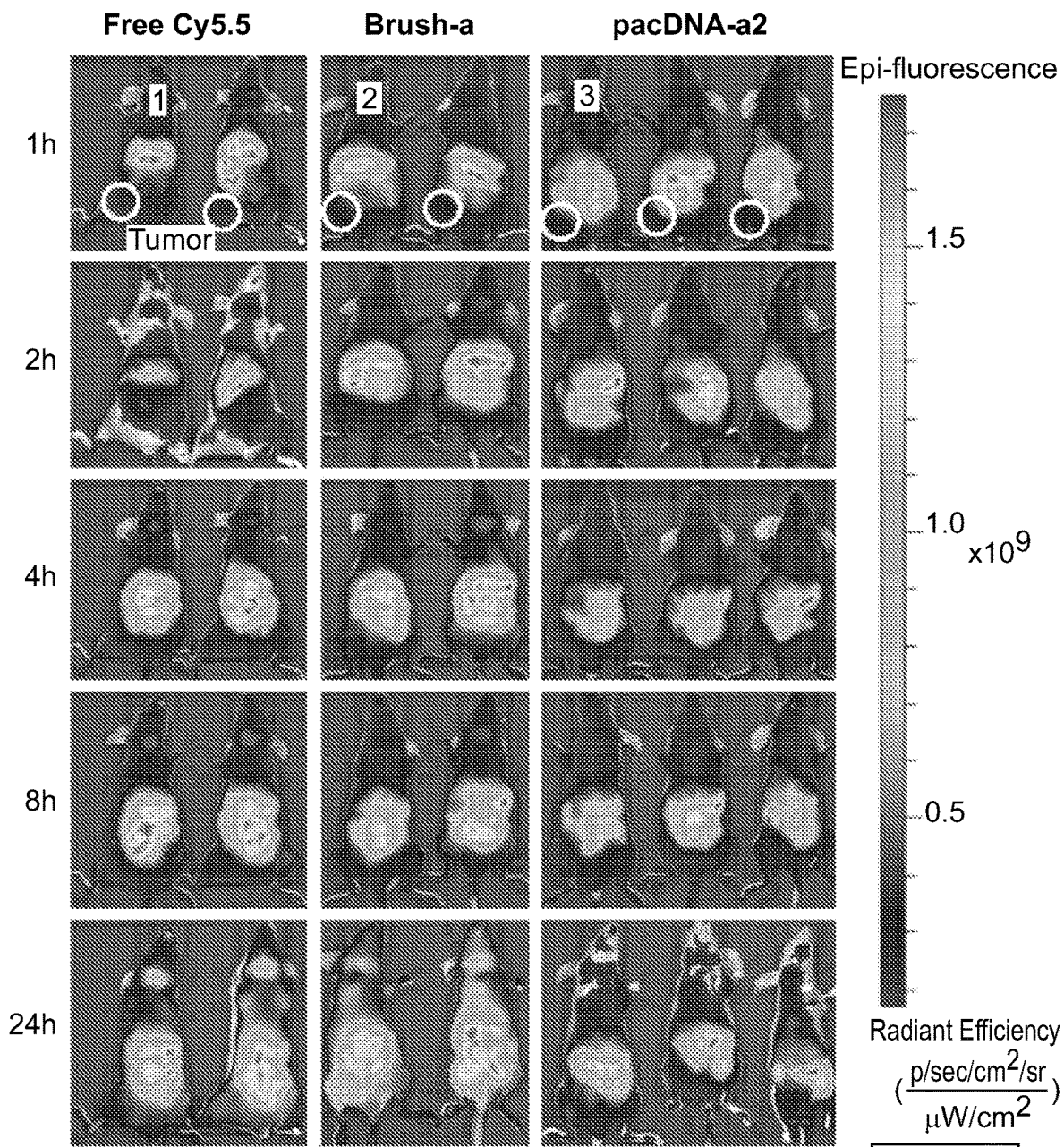
FIG. 5A: Near IR-imaging over 24 h (Cy5.5 channel) of live mice injected in the tail vein with free Cy5.5, brush-a, and pacOligo-a2. (B) Ex vivo imaging of tissues from numbered mice (T-tumor; H-heart; Lg-lung; K-kidney; S-spleen; Lv-liver).
Figure 5B:
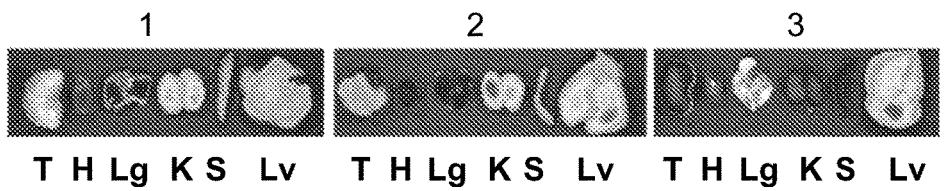

Because the physical size of the brush can be tuned by controlling the degree of polymerization and side-chain length, it is possible for pacOligo to take advantage of the enhanced permeation and retention effect (EPR) for passive cancer targeting. Being able to target cancer via EPR would necessitate sufficient blood circulation times, which in turn require appropriate pacOligo size (10-100 nm) and low opsonization of the pacOligo surface. PacOligo-c1 and -a2 are used to study in vivo biodistribution, because these two structures provide a contrast in protein shielding capabilities. To enable in vivo imaging, a near-infra red tag (Cy5.5) is incorporated into the pacOligo by consuming a small amount of the brush NHS ester groups (<10% by mol). The DNA component is modified with a Cy3 tag (DNA-1': 5'-NH$_2$-CCC AGC CCT C-Cy3-3')(SEQ ID NO.: 6) to allow for independent tracking. As an animal model, xenograft mice with orthotopically implanted mouse breast cancer cells (4T1) in the right mammary fat pad are used. In addition to pacOligos, free dye, free DNA, and brush polymers are used as controls. For pacOligo-c1 and its parent polymer (brush-c), it can be seen that the nanostructures appear gradually on the surface of the mice after 2 h and persists for 24 h (after which mice are sacrificed), suggesting good blood circulation (FIG. 4A). Significant tumor uptake is also evident in images obtained after 8 h, which is con-firmed by ex vivo imaging of tissues at 24 h (FIG. 4B). Images of both Cy3 and Cy5.5 channels show that the signals from the DNA and the polymer components are colocalized in the tumor and other organs, indicating that the pacOligo nanostructure remains intact. In contrast, lacking the shielding effect from the brush polymer, free DNA is rapidly cleared by the liver. On the other hand, pacOligo-a2 shows primarily hepatic uptake and minimal tumor accumulation, while its parent polymer (brush-a) shows moderate levels of tumor uptake, but is largely cleared by the kidney (FIG. 5). One interpretation of these results is that pacOligo-a2 does not have sufficient shielding of the DNA, and the exposed DNA leads to the recognition and capture by liver endothelial cells. For the parent polymer brush-a, which has a Mn of only 76.3 kDa, renal clearance via glomerular filtration is possible. These data are consistent with the fluorescence-based protein accessibility analyses (vide supra), and suggest that, when designed appropriately, the pacOligo is a viable platform for systemic oligonucleotide delivery.

Examples 3-5

In the following examples, an antisense pacOligo having 10 kDa PEG side chains that targets the human epidermal growth factor receptor 2 (Her2) mRNA (pac-DNA$_{10k}$, Scheme 1) was made. Her2 is an important biomarker for many cancers including several types of breast, stomach and ovarian cancers, and antisense control of the Her2 gene has been previously demonstrated. For controls, an improper pacOligo with overly short side chains (5 kDa), and a Y-shaped PEG-DNA conjugate ($_Y$PEG-DNA) were used.

The pacOligo5 k is incapable of effectively protecting the embedded oligonucleotide against enzymatic degradation. The YPEG is routinely used to form bioconjugates and is found in a commercial oligonucleotide drug formulation (Macugen). However, because of the low density of the PEG chains (2 chains), adequate enzymatic protection to the DNA was not obtained.

Materials and Methods for Examples 3-5

Phorsphoramidites and supplies for DNA synthesis were purchased from Glen Research Co. ω-Amine polyethylene glycol (PEG) methyl ether (Mn=5, 10 kDa, PDI=1.05) and Y shaped PEG NHS ester (Mn=40 kDa, PDI=1.05) were purchased from JenKem Technology USA. Dulbecco's Modified Eagle Medium (DMEM) was purchased from Sigma-Aldrich CO. Mouse 4T1 and human SKOV3 cancer cell line were purchased from American Type Culture Collection (Rockville, Md., USA). All other common materials were purchased from Sigma-Aldrich Co., VWR International LLC., or Fisher Scientific Inc., and used without further purification unless otherwise indicated. DLS and zeta potential data were acquired on a Malvern Zetasizer Nano-ZSP (Malvern, UK). MALDI_ToF MS measurements were carried out on a Bruker Microflex LT mass spectrometer (Bruker Daltonics Inc., Mass., USA). UV-Vis data were obtained on a Cary 4000 UV-Vis spectrophotometer (Varian Inc., Calif., USA). Fluorescence spectroscopy was performed on a Cary Eclipse fluorescence spectrophotometer (Varian Inc., Calif., USA). 1H and 13C NMR spectra were recorded on a Varian 400 MHz NMR spectrometer (Varian Inc., Calif., USA). Chemical shifts (δ) were reported in ppm. Infrared (IR) spectra were obtained on a Bruker Tensor FT-IR spectrometer (Bruker Corporation, Mass., USA). N,NDimethylformamide (DMF) GPC was carried out on a TOSOH EcoSEC HLC-8320 GPC system (Tokyo, Japan) equipped with a TSKGel GMHHR-H, 7.8×300 mm column and RI/UV-Vis detectors. HPLC-grade DMF with 0.04 M LiBr was used as the mobile phase, and samples were run at a flow rate of 0.5 mL/min. GPC calibration was based on polystyrene standards (706 kDa, 96.4 kDa, 5970 Da, 500 Da). Aqueous GPC measurements were performed on a Waters Breeze 2 GPC system equipped with an Ultrahydrogel™ 500, 7.8×300 mm column and a 2998 PDA detector (Waters Co., Mass., USA). Sodium nitrate solution (0.1 M) was used as the eluent running at a flow rate of 0.8 mL/min. Reverse-phase HPLC was performed using a Waters Breeze 2 HPLC system coupled to a Symmetry® C18 3.5 µm, 4.6×75 mm reverse phase column and a 2998 PDA detector, using TEAA buffer (0.1 M) and HPLC-grade acetonitrile as mobile phases. TEM samples were imaged on a JEOL JEM 1010 electron microscope utilizing an accelerating voltage of 80 kV.

Synthesis of Monomers

Compound 1. In a round bottom flask, 2.0 g (20.6 mmol) of maleimide and 1.54 g (22.6 mmol) of furan were dissolved in 20 mL ethyl acetate. The solution was refluxed for 4 h, and a white solid, compound 1, precipitated from the reaction mixture during the course of the reaction. The solids were isolated by filtration, washed with ethyl ether, and dried under vacuum.

$^1$H-NMR (400 MHz, CDCl$_3$): δ8.14 (s, 1H, —CNHC—), 6.52 (s, 2H, CH═CH), 5.31 (s, 2H, CHOCH), 2.99 (s, 2H, CH—CH); $^{13}$C-NMR (400 MHz, CDCl$_3$): δ176.2, 136.8, 81.2, 48.9.

Compound 2. 2.59 g (12 mmol) of 1,4-dibromobutane, 2.07 g of K$_2$CO$_3$ (15 mmol), and 5 mL DMF were added to a round bottom flask, to which a solution of 1 (0.5 g, 3 mmol) in 5 mL DMF was added dropwise over a period of 30 min with stirring. The reaction mixture was allowed to stir overnight at room temperature. Silica gel chromatography (3:1 v:v hexane:EtOAc) was used to purify 2. Upon drying under vacuum, compound 2 appears as a white solid.

$^1$H-NMR (400 MHz, CDCl$_3$): δ6.51 (s, 2H, CH═CH), 5.26 (s, 2H, CHOCH), 3.51 (t, 2H, NCH$_2$), 3.41 (t, 2H, CH$_2$Br), 2.84 (s, 2H, CH—CH), 1.84-1.71 (m, 4H, CH$_2$—CH$_2$); $^{13}$CNMR (400 MHz, CDCl$_3$): δ176.5, 136.8, 81.2, 47.6, 38.1, 33.1, 29.8, 26.4.

Oligonucleotide Synthesis

Oligonucleotides were synthesized on a Model 391 DNA synthesizer (Applied Biosystems, Inc., Foster City, Calif.) using standard solid-phase phosphoramidite methodology. Oligonucleotides were purified by reverse-phase HPLC liquid chromatography. All DNA strands were cleaved from the CPG support using aqueous ammonium hydroxide (28-30% NH$_3$ basis) at room temperature for 48 h. The dimethoxytrityl (DMT) protecting group was removed by treatment with 20% acetic acid in H$_2$O for 1 h, followed by extraction with ethyl acetate for three times. The successful syntheses of all DNA sequences were verified by MALDI-ToF MS.

General Method for Synthesizing Brush Copolymers

Norbornenyl PEG (N-PEG) was synthesized according to a previously reported method. (Lu et al., J. Am. Chem., 2014, 136, 10214). Modified 2nd generation Grubbs' catalyst was synthesized based on a published protocol. (Love et al., Angew. Chem. Int. Ed., 2002, 41, 4035). The catalyst (0.02 M) was dissolved in DCM in a 5 mL Schlenk flask. The monomers (0.04 M) were each dissolved in DCM in 5 mL Schlenk flasks. All reagents were separately degassed by 3× freeze-pump-thaw cycles. The flask containing norbornenyl bromide (N—Br, 5 equiv.) was cooled to −20° C. by using an ice-salt bath, and the stock solution containing modified Grubbs' catalyst (1 equiv.) was added via a microsyringe. The reaction mixture was stirred for 30 min (TLC shows complete consumption of the NBr), before the second monomer, N-PEG (30 equiv.), was added. The reaction mixture was further stirred for 6 h. At the end of the reaction, several drops of ethyl vinyl ether (EVE) were added to the mixture and the reaction was stirred overnight. The mixture was then concentrated and precipitated into ethyl ether 3× and the precipitant was dried in vacuo. The polymer was then allowed to react with excess NaN$_3$ in DMF overnight at room temperature, and was dialyzed against Nanopure™ water for 24 h. Thereafter, the polymer was injected into an aqueous GPC column, and the fractions containing the polymer were collected, combined, concentrated, and was further desalted by a NAP-10 column. Infrared spectroscopy showed successful incorporation of azide groups.

Quantitation of the Azide Groups in Brush Polymers

In a 1.5 mL microcentrifuge tube, brush polymer (5 nmol) was dissolved in 200 µL Nanopure™ water, to which fluorescein-alkyne (Lumiprobe, 0.207 mg, 500 nmol), copper(II) sulfate pentahydrate (CuSO$_4$.5H$_2$O, 500 nmol, 5 µL 100 mM aqueous solution), Tris(3-hydroxypropyltriazolylmethyl)amine (THPTA, 600 nmol, 6 µL 100 mM aqueous solution), and sodium ascorbate (2.5 µmol) were added. The reaction mixture was shaken on an Eppendorf shaker at room temperature overnight, before being dialyzed against a NaCl solution (0.15 M) using dialysis tubing with a MWCO of 6-8 kDa for 48 h. The UV-Vis absorption of the polymer solution at 491 nm was measured and compared with a standard curve. The number of fluorescein molecules per polymer was calculated based on the known polymer concentration. Approximately 5.5 and 5.8 fluorescein tags were attached to brush$_{5k}$ and brush$_{10k}$, respectively.

General Method for PacOligo Synthesis

Azide-brush polymers were dissolved in aqueous NaCl solution (2 M) to give a final concentration of 0.1 mM. DBCO-modified DNA (60 nmol) was dissolved in 200 µL aqueous NaCl solution (2 M). The polymer solution (40 µL) was added to the DNA solution, and the mixture was shaken gently for 48 h at 40° C. on an Eppendorf Thermomixer. The reaction mixture was then dialyzed against Nanopure™ water using a MINI dialysis unit (MWCO 3500 Thermo Fisher) for desalting. The dialysate was further subjected to aqueous GPC purification. The fraction containing the conjugate was collected and dialyzed against Nanopure™ water to remove NaNO3. The final solution was lyophilized to yield a white powder (or green/red powders for fluorescein and Cy3 labeled conjugates).

Synthesis of $_y$PEG-DNA

Y-shaped PEG NHS ester (80 mg, 2 µmol), 3-azido-1-propanamine (N$_3$-amine, 0.16 mg, 1.6 µmol), and N, N-diisopropylethylamine (0.65 mg, 5 µmol) were added to a 25 mL round bottom flask. The reaction was vigorously stirred for 30 min. TLC shows complete consumption of N$_3$-amine. Then, another 0.16 mg (1.6 µmol) of N3-amine was added and the reaction mixture was allowed to stir for 1 h before being precipitated into diethyl ether 3×. The product was dried under vacuum and further purified by a NAP-10 column to remove impurities. The final solution was lyophilized to give a white powder. To synthesize $_y$PEG-DNA conjugate, 2 mg (50 nmol) of Y-shaped PEG azide was combined with 60 nmol DBCO-modified DNA strands in 200 µL Nanopure™ water. The reaction mixture was shaken at 40° C. for 48 h and purified by aqueous GPC. To achieve baseline separation between conjugate and free DNA, three Waters Ultrahydrogel™ 500 columns were used in tandem combination. After purification, the conjugate was desalted by a NAP-10 column and was lyophilized to yield a white powder (or green/red powders for fluorescein and Cy3-labeled conjugates).

Hybridization Kinetics Assay

Free DNA, $_y$PEG-DNA, and pacOligo (all fluorescein-labeled) were each dissolved in microcentrifuge tubes in PBS buffer (pH=7.4) to give a final concentrations of 100 nM. Each solution (1 mL) was transferred to a fluorescence cuvette, to which a complementary dabcyl-DNA strand or a non-complementary strand (2 equiv.) was added via 1 µL of PBS solution. The fluorescence of the mixture (ex=490 nm, em=520 nm) was monitored before mixing and every 3 sec thereafter for 60 min using a Cary Eclipse fluorescence spectrometer.

The endpoint is determined by adding a large excess of complementary dabcyl-DNA to the mixture followed by incubation for an extended period of time (>1 h). The kinetics plots are normalized to the end point determined for each sample.

Nuclease Degradation Kinetics Assay

Free DNA, $_y$PEG-DNA and pacOligo (1 µM, all fluorescein-labeled) were each mixed with their respective complementary dabcyl-labeled DNA (2 µM) in PBS buffer. The mixtures were heated to 80° C. and allowed to cool slowly to room temperature in a thermally insulated container during a period of 10 h. The mixtures were then diluted to 100 nM in assay buffer (10 mM tris, 2.5 mM MgCl$_2$, and 0.5 mM CaCl$_2$, pH=7.5), and 1 mL of each mixture was transferred to a fluorescence cuvette which was mounted on a fluorimeter. DNase I (Sigma-Aldrich) was then added and rapidly mixed to give a final concentration of 0.1 unit/mL. The fluorescence of the samples (ex=490 nm, em=520 nm) was measured immediately and every 3 secs for 6 h. The endpoint was determined by adding a large excess of DNase I (ca. 2 units/mL) to the mixture, and the fluorescence was monitored until no additional increase was observed. The kinetics plots were normalized to the endpoints determined for each sample, and all experiments were performed in triplicates.

Synthesis of Anti-Her2 SNA

In a typical synthesis, 60 nmol of thiol modified antisense DNA strands were treated with 100 µL of 100 mM dithiothreitol (DTT) in 50 mM pH 8.0 phosphate buffer for 0.5 h and desalted using a NAP-10 column. These purified strands were then added to 15 mL of gold nanoparticles (13 nm, 10 nM, synthesized via a literature method) pre-mixed with 15 µL of 10% TWEEN 20. The mixture was then heated to 50° C. in an Eppendorf Thermomixer for 2 h. Over 10 h, the particles were brought to an elevated salt concentration (0.5 M) by adding aliquots of 5 M NaCl. The particles were shaken for an additional 48 h at 50° C. on an incubator shaker. Particles were then purified by centrifugation and resuspensed in Nanopure™ water. This process was repeated 3×. After the final centrifugation, SNA particles were resuspended in 15 mL of PBS buffer containing 0.01% TWEEN 20.

Cell Culture

Human SKOV3 and mouse 4T1 cells were grown in DMEM medium with 10% heat inactivated fetal bovine serum, 1% antibiotics, 1% L-glutamine, and were maintained at 37° C. in 5% CO$_2$.

Confocal Fluorescence Microscopy

To study the cellular uptake of pacOligo, 4T1 or SKOV3 cells were seeded at a density of $1.0 \times 10^5$ cells/well in 24-well glass bottom plates and were cultured overnight at 37° C. and 5% CO$_2$. Serum-free DMEM containing Cy3-labeled free DNA or Cy3-labeled pacOligo$_{10k}$ at equal doses of DNA (100 nM) were added to each well, followed by incubation for 6 h at 37° C. The cells were then gently washed with PBS 3×, fixed with a 4% formaldehyde solution for 15 min, and stained with 10 µM DAPI for 3 min. The cells were imaged on an LSM-700 confocal laser scanning microscope (Carl Zeiss Ltd., Cambridge, UK) at excitation wavelengths of 408 nm (DAPI) and 543 nm (Cy3). Imaging settings were identical for free DNA- and pacOligo-treated cells.

Flow Cytometry

SKOV3 cells were seeded at a density of $2.0 \times 10^5$ cells/well in a 6-well plate and were cultured overnight at 37° C. and 5% CO2. Serum-free DMEM medium containing Cy3labeled free DNA, $_y$PEG-DNA, pacOligo$_{5k}$, and pacOligo$_{10k}$ (100 nM equivalent of DNA) were added to each well, followed by further incubation for 6 h. The cells were washed with PBS 3×, harvested by trypsinization, and transferred into fluorescence activated cell sorter tubes. All samples were analyzed by flow cytometry (FACS Calibur, BD Bioscience, San Jose, Calif.) to determine the extent of cellular internalization.

Quantification of Cell Uptake

Figure 6:
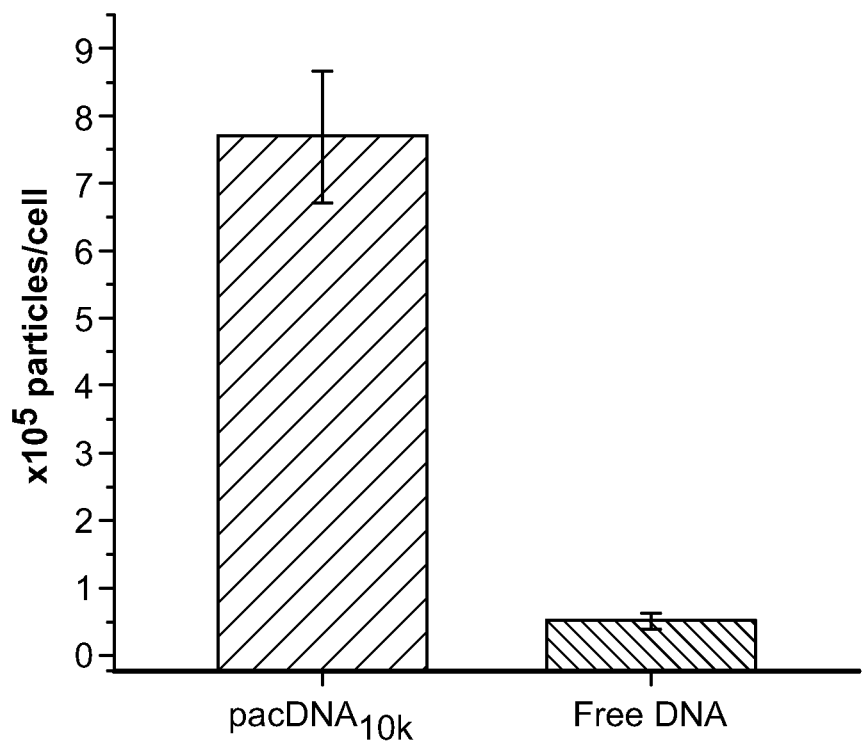
FIG. 6: Quantification of cell uptake in SKOV3 cells. Cells were incubated with fluorescein-labeled free DNA or pacOligo$_{10k}$ (1 µM DNA concentration).

SKOV3 cells were seeded at a density of $2.0 \times 10^5$ cells/well in a 24-well plate and were cultured overnight. Serum-free DMEM medium containing fluorescein-labeled free DNA and pacOligo$_{10k}$ (1 µM equivalent of DNA) were added to each well, followed by further incubation for 6 h. The cells were washed with PBS 3×, harvested by trypsinization, and were counted using a TC20™ automated cell counter (Bio-Rad, Mass., USA). The cells were then centrifuged, lysed with 100 µL RIPA Cell Lysis Buffer, and transferred to a 96-well plate. The fluorescence of each cell lysate was determined by a microplate reader (Biotek Synergy HT, BioTek Instruments, Inc. Vt., USA) and was compared with a fluorescein standard curve, created by serial dilution of fluorescein-labeled free DNA in RIPA buffer). The number of DNA strands per cell was calculated based on Equation 1. There are ca. $7.7 \pm 1.0 \times 10^5$ particles in pacOligo$_{10k}$-treated samples and ca. $0.51 \pm 0.16 \times 10^5$ DNA strands in free DNA-treated samples, respectively (FIG. 6).

$$pacDNA/cell = \frac{\text{Concentration of DNA} \times \text{Volume of lysate} \times \text{Avogadro's Constant}}{\text{Number of cells per well} \times \text{Number of DNA strands per } pacDNA}$$

MTT Assay

The cytotoxicity of pacOligo was evaluated with the MTT assay. Briefly, SKOV3 or 4T1 cells were seeded in a 96-well plate in 100 μL medium and cultured for 24 h. The cells were then treated with free DNA, free brush$_{10k}$, and pacOligo$_{10k}$ at varying concentrations of total DNA (0.1, 0.25, 0.5, 1 and 4 μg). Lipofectamine 2000 (Invitrogen) was used as a positive control using conditions suggested by the manufacturer. Cells treated with PBS were used as a negative control. After 48 h, 3-[4,5-dimethylthiazol-2-yl]-3,5diphenyltetrazolium bromide (MTT dye, final concentration of 0.5 mg/mL) was added. The cells were incubated for 4 h and the absorbance was measured at 570 nm using a microplate reader (Biotek Synergy HT).

Western Blotting

SKOV3 cells were plated in 6-well plates at a density of $2.0 \times 10^5$ cell per well and cultured overnight. Cells were incubated with free DNA, free brush$_{10k}$, $_y$PEG-DNA, pacOligo$_{5k}$, scrambled pacOligo$_{10k}$, pacOligo$_{10k}$ (10 nM, 100 nM, 1000 nM), and Lipofectamine-complexed DNA in opti-MEM. The incubation concentration of all samples except pacOligo$_{10k}$ was 100 nM (DNA concentration). After 20 h, the medium was replaced with fresh, full growth medium and cells were cultured for another 48 h. Whole cell lysates were prepared in 100 μL of RIPA Cell Lysis Buffer with 1 mM phenylmethanesulfonylfluoride (PMSF, Cell Signaling Technology) according to the manufacturer's suggested protocol. Protein concentrations were determined using a BCA Protein Assay Kit (Pierce). Equal amounts (5 μg) of protein samples were fractionated by 4-20% SDS-PAGE and transferred to PVDF membrane, and were analyzed by Western blotting with Her2 and GAPDH antibodies (Invitrogen) using an ECL Western Blotting Substrate (Pierce).

Example 3

Figure 7:
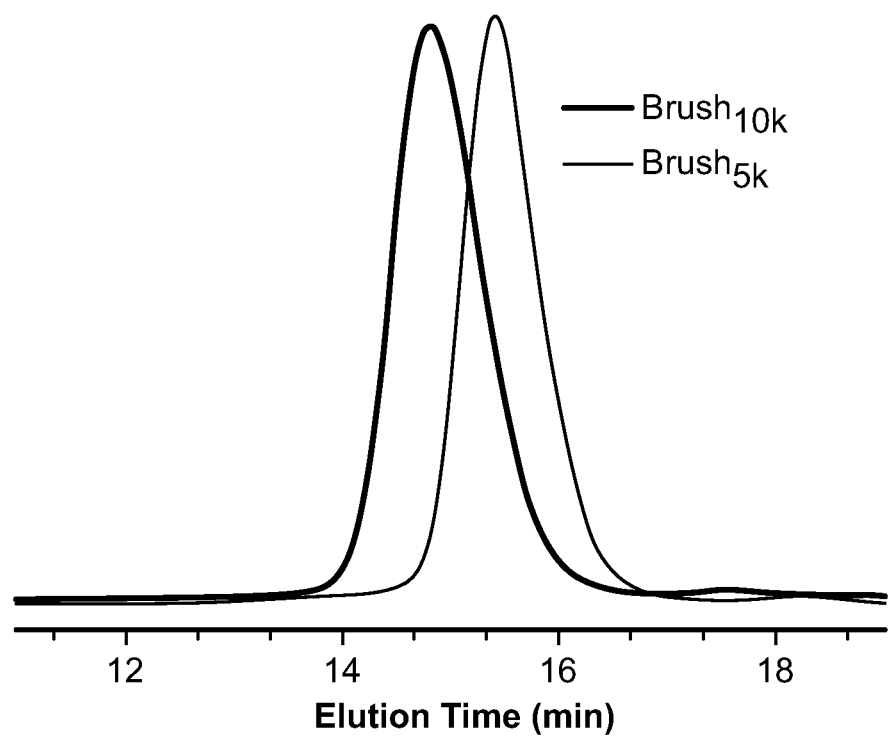
FIG. 7: DMF GPC chromatograms of brush polymer $10_k$ and brush polymer $_{5k}$.

In Examples 1 and 2, the pacOligo structure was synthesized by coupling amine-modified DNA to diblock brush polymer containing N-hydroxyl succininimide (NHS) groups in an aqueous bicarbonate buffer. The reaction efficiency is affected by the hydrolysis of NHS groups, requiring the use of large excesses (>20:1 mol:mol) of the DNA. For the following study, cyclooctyne-mediated copper-free click chemistry was used in place of the amidation reaction, resulting in near-quantitative yields. To achieve the coupling, a Her2 antisense DNA strand is modified with 5' dibenzocyclooctyne (DBCO) group (sequence: 5' DBCO CTC CAT GGT GCT CAC TTT 3' (SEQ ID NO.: 8)), while the brush polymer bears the azide groups. The brush polymers are synthesized via sequential ring opening metathesis polymerization (ROMP) of norbornenyl bromide (N—Br) and norbornenyl PEG (N-PEG, Mn=5 or 10 kDa, PDI<1.05), followed by azide substitution of the bromide. The resulting brush is of a diblock structure, with the first, oligomeric block (~5 repeating units) serving as a reactive region for DNA conjugation, and the second, longer block (~30 repeating units) creating the brush architecture and the steric congestion needed to protect the DNA. Dimethylformamide gel permeation chromatography (DMF GPC) shows narrow molecular weight distribution (PDI<1.15) for the brush polymers (FIG. 7), and the successful incorporation of the azide group is verified by infrared spectroscopy, which shows characteristic vibration of the azido group at 2029 cm$^{-1}$.

TABLE 4

Oligonucleotide sequences used in Examples 3-5

| | |
|---|---|
| Her2 Antisense | 5'-DBCO-TTT CTC CAT GGT GCT CAC-3' (SEQ ID NO.: 8) |
| Fluorscein-labeled Her2 Antisense | 5'-DBCO-TTT CTC CAT GGT GCT CAC-fluorescien-3' (SEQ ID NO.: 9) |
| Cy3-labeled Her2 Complementary strand | 5'-DBCO-TTT CTC CAT GGT GCT CAC-Cy3-3' (SEQ ID NO.: 11) |
| Dabcyl-labeled Her2 Complementary strand | 5'-Dabcyl-GTG AGC ACC ATG GAG-3' (SEQ ID NO.: 10) |
| Dabcyl-labeled Scrambled Sequence | 5'-NH$_2$-TTT ACT-dabcyl AAC CTT TCC GTC GCA GCA AAA-3' SEQ ID NO.: 5) |
| Scrambled Her2 Antisense | 5'-DBCO-TTT TAA CTC TGA CAT GAT GTC-3' (SEQ ID NO.: 12) |
| Her2 Antisense on SNA | 5'-CTC CAT GGT GCT CAC T$_{(10)}$-SH-3' (SEQ ID NO.: 13) |

Figure 9:
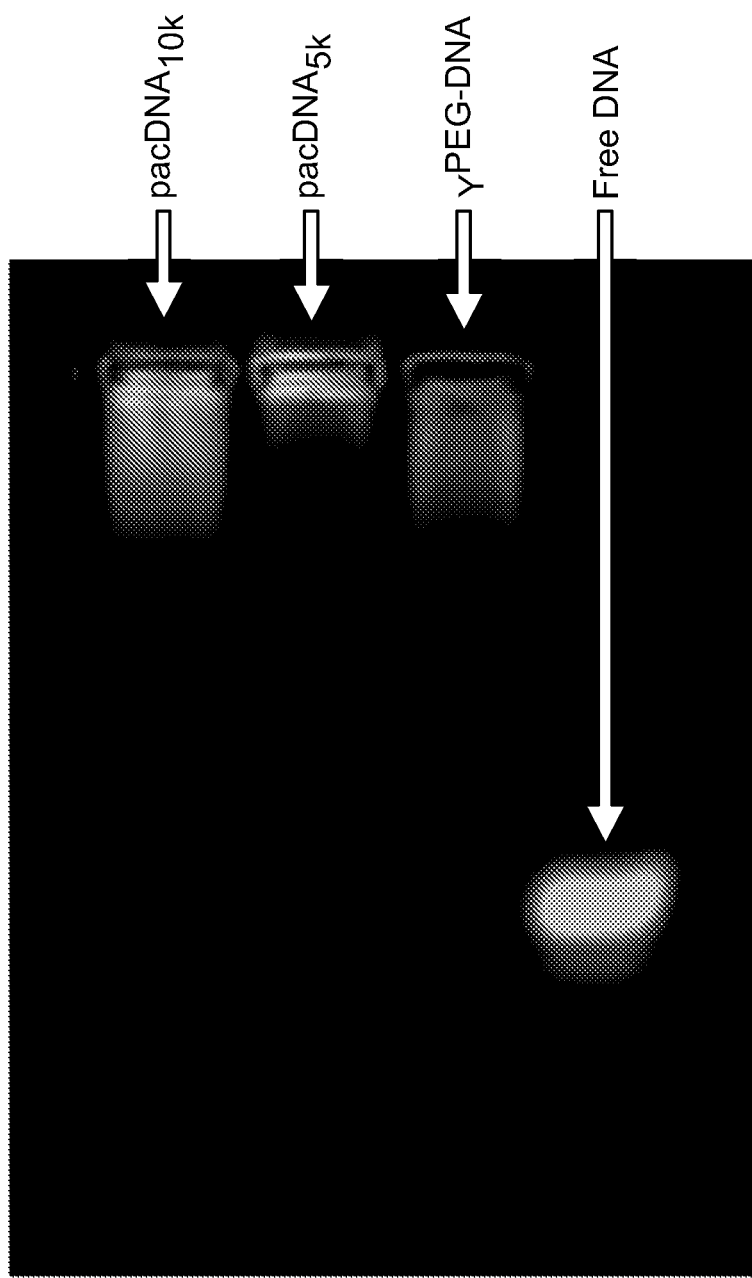
FIG. 9: Agarose gel (1%) electrophoresis of fluorescein-labeled pacOligo$_{10k}$, pacOligo$_{5k}$ and γPEG-DNA and free DNA.
Figure 10A:
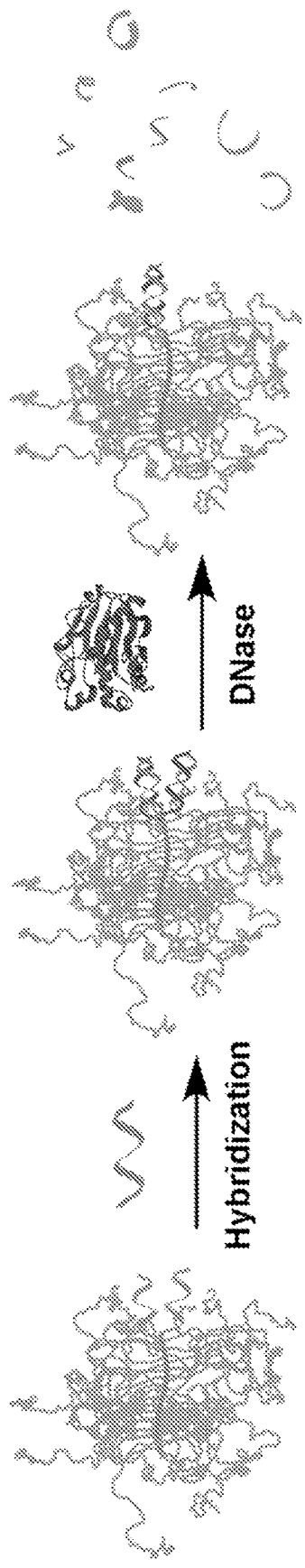
FIG. 10A-C: (A) Schematics of DNA hybridization and DNase I degradation assays. (B-C) Hybridization and degradation kinetics of pacOligos, γPEG-DNA, and free DNA.
Figure 10C:
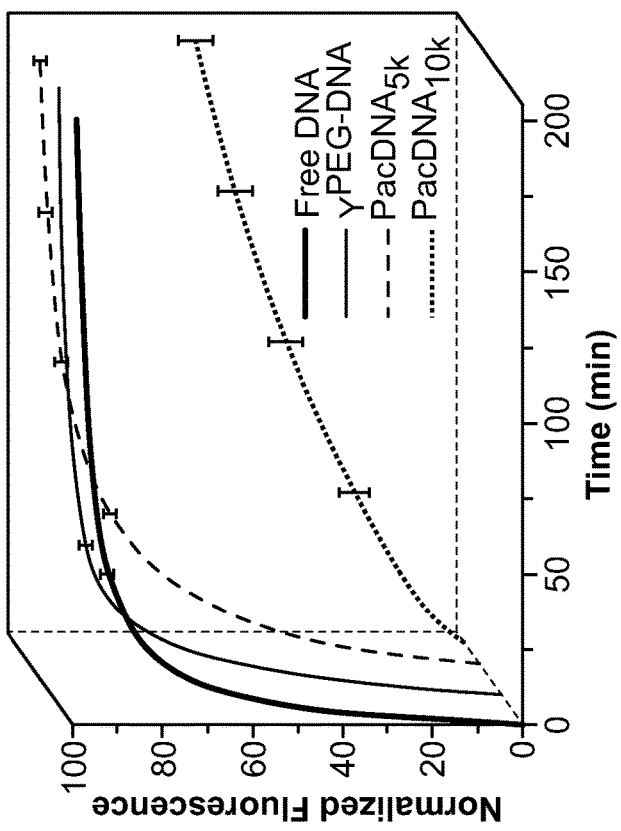
Figure 12:
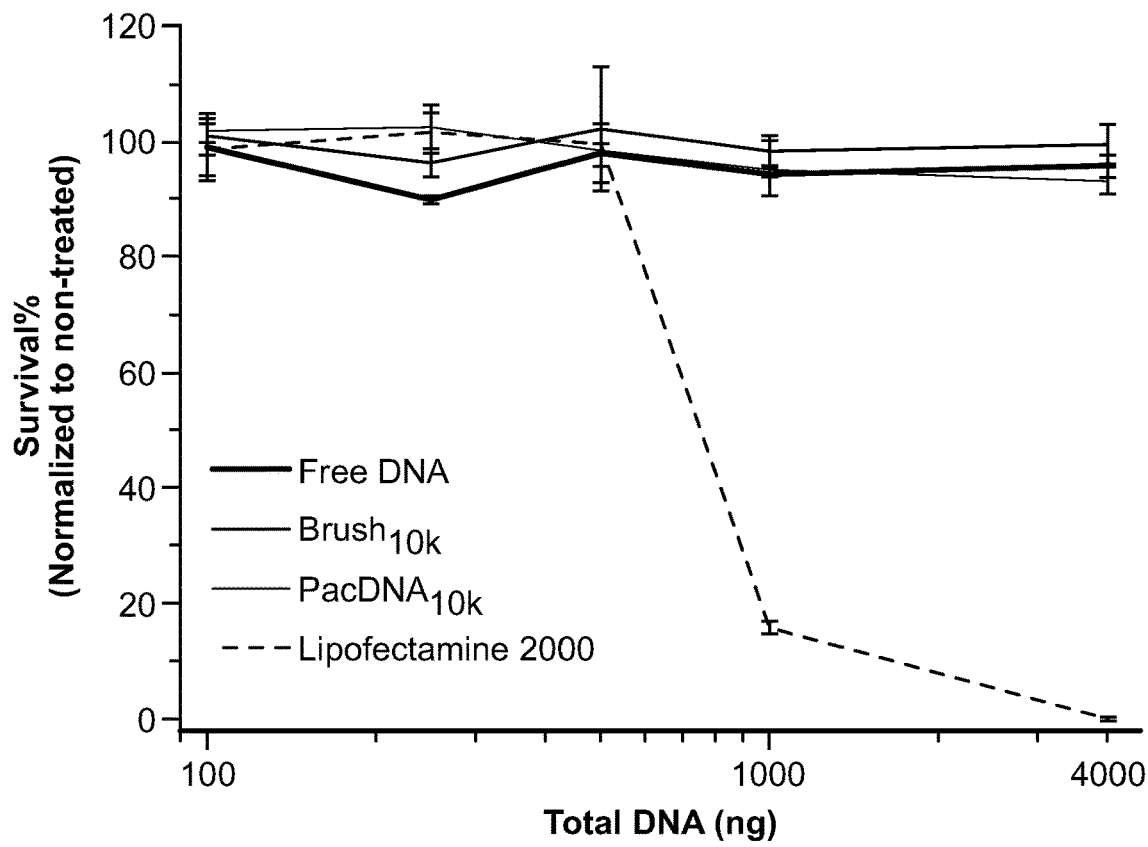
FIG. 12: MTT cytotoxity assay for free DNA, brush$_{10k}$, pacOligo$_{10k}$, and Lipofectamine2000-complexed DNA in mouse 4T1 cells.

Coupling of the DBCO-modified DNA strand to the brush polymers and the YPEG is achieved by incubation in 2 M NaCl solution at 40° C. for 48 h (3:1 alkyne:azide mol:mol). The elevated salt concentration is used to achieve high DNA loading by screening the charge between DNA strands. Purified conjugates are free of unconjugated DNA as shown by aqueous GPC and agarose gel electrophoresis (FIG. 8(A)

and FIG. 9). The numbers of DNA strands per brush is determined by peak integration of the GPC chromatograms recorded at 488 nm to be 5.7 and 4.9 for pacOligo$_{10k}$ and pac-DNA5 k, respectively (FIG. 10). The pacOligo exhibits a spherical morphology, with a dry-state diameter of 18.2±2.5 for pacOligo$_{5k}$ and 21.9±3.1 nm for pacOligo$_{10k}$, as evidenced by transmission electron microscopy (TEM) (FIGS. 8E and F. These measurements are consistent with dynamic light scattering analysis, showing number-average hydrodynamic diameters of 17.0±4.2 nm and 23.7±5.9 nm for the 5 k and 10 k pacOligos, respectively (FIGS. 8C and 8D). Zeta potential measurements indicate that pacOligos and the $_Y$PEG-DNA have significantly reduced negative surface charge (from −9.8 mV to −20.3 mV) compared with free DNA in Nanopure water (−47.4 mV, FIG. 12B) (FIG. 8B), which is expected from the dilution of surface charge for the conjugates.

Figure 10B:
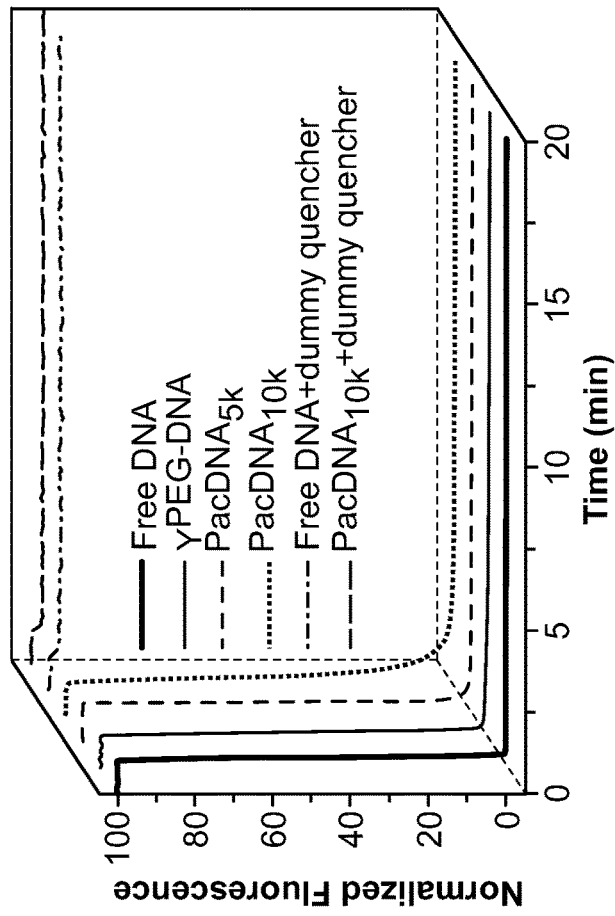

The ability of the DNA conjugates to hybridize with complementary strands and resist nuclease degradation is compared. Hybridization is monitored by a fluorescence quenching assay, where a quencher (dabcyl)-modified complementary strand is added to fluorescein-labeled conjugates. The rate of fluorescence decrease is a direct indicator of the hybridization kinetics (FIG. 10A). Remarkably, both pac-DNAs and the $_Y$PEG-DNA hybridize rapidly with complementary DNA (t1/2<10 s), with negligible difference compared with free DNA (FIG. 10B). When a dummy (non-complementary) dabcyl-DNA strand is added, fluorescence intensities are not affected, ruling out non-hybridization interactions. In order to probe the extent of nuclease protection, DNase I is added to fluorescein-labeled DNA conjugates that are pre-hybridized to dabcyl-modified complementary strands. Upon DNase I action, the fluorophore is released, which leads to an increase of fluorescence (FIG. 10A). The pacOligo$_{10k}$ exhibits significantly extend half-life (t1/2) of ~141.9 min compared with free DNA, which is degraded rapidly with a t1/2 of ~6.0 min. On the other hand, pacOligo$_{5k}$ has very limited protective power, showing a t1/2 of ~13.2 min. This is not surprising because the fluorophore is located at the periphery (3') of the DNA; once the DNA extends beyond the PEG shell of the brush, the exposed portion should experience a rapid drop-off in steric protection. Similarly, the YPEG barely lends any protection to conjugated DNA, with a t1/2 of ~8.2 min, despite having twice the length of the side chains of pacOligo$_{10k}$. These results show that both the brush side chain length and steric congestion created by a densely grafted architecture can be readily selected to provide oligonucleotides with steric selectivity.

Example 4

Figure 11A:
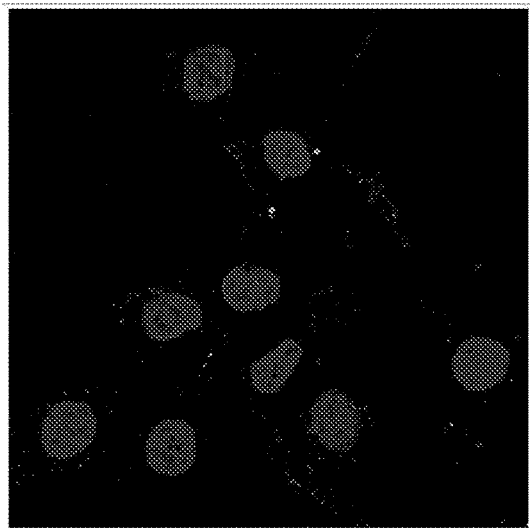
FIG. 11A-D: Confocal fluorescence microscopy images of SKOV3 cells incubated with 100 nM of free Cy3-DNA (A) or Cy3 pacOligo$_{10k}$ (B). Cell nuclei were stained with DAPI (blue). Scale bar is 20 µm. (C) Flow cytometry measurements of cells treated with 100 nM Cy3-labeled samples. (D) MTT cytotoxity assay for SKOV3 cells.
Figure 11B:
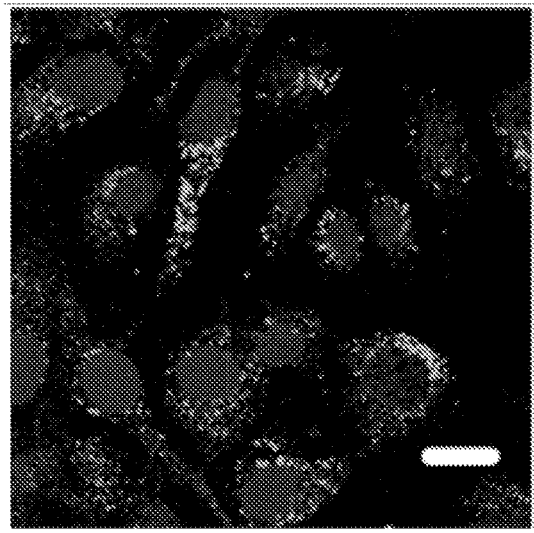
Figure 11C:
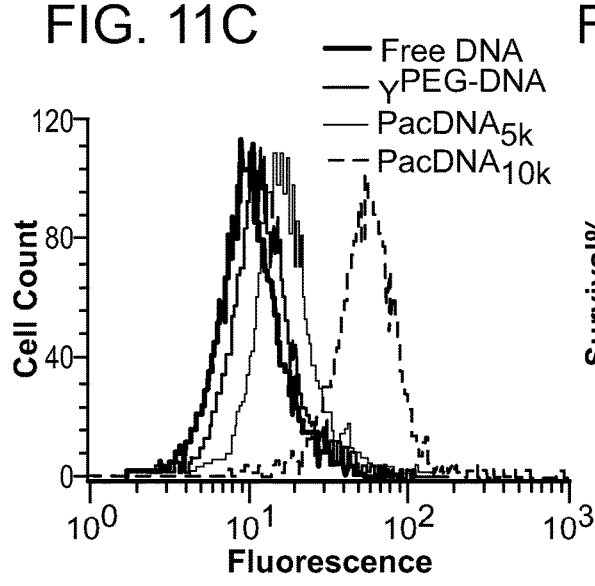
Figure 11D:
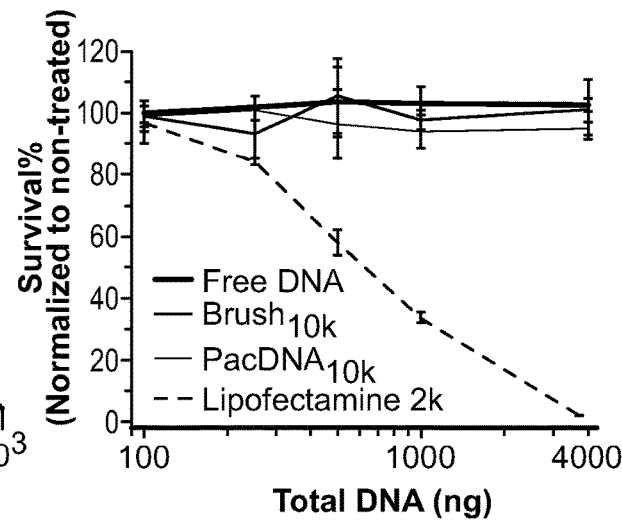

In order for the pacOligo to serve as an antisense agent, it needs to efficiently enter cells. Cell uptake efficiency is evaluated in SKOV3, a human ovarian cancer line. To enable tracking, conjugates are labeled at the DNA component with the fluorophore Cy3. Cells are incubated with the conjugates and free DNA for 6 h, followed by flow cytometry analysis. Interestingly, cell uptake appears to be a function of DNA accessibility; the better hidden the DNA, the greater the cell uptake (FIG. 11C). This is an advantageous phenomenon because DNA accessibility is inversely correlated with nuclease stability. Confocal microscopy confirms the cell uptake of the pacOligo. As shown in the FIG. 11A, B and FIG. 12), free DNA-treated cells produce very small amount of fluorescence signals, while the same concentration of DNA, when packaged into pacOligo$_{10k}$, results in much stronger fluorescence signals under identical imaging settings. Quantification using cell lysates shows that there are ca. 7.7×10$^5$ pac-DNA10 k particles/cell when the cells are incubated with an equivalent of 1 µM of DNA for 6 h (FIG. 6).

Example 5

Figure 13:
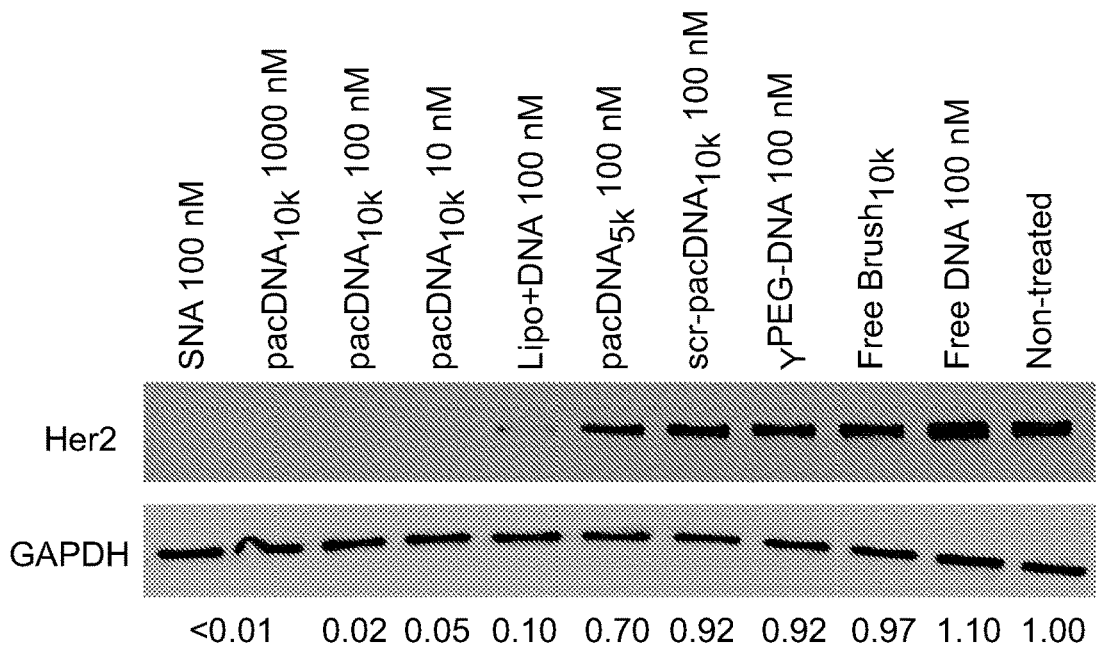
FIG. 13: Western blot analysis of pacOligos and controls.

Having demonstrated that the pacOligo has improved cell uptake, the antisense activity towards Her2 in SKOV3 cells, which is a Her2-overexpressing cell line, is analyzed. For positive controls, Lipofectamine, an effective cationic liposomal transfection agent, and SNAs with 13 nm gold nanoparticle cores bearing identical antisense strands, are used. PacOligo$_{10k}$ containing a scrambled sequence and brush polymers devoid of DNA strands are used as negative controls. SKOV3 cells were treated with samples and controls at varying concentrations (10-1000 nM DNA) for 20 h, followed by culturing for another 48 h in fresh media. The total cellular protein for each sample is harvested and analyzed by western blot. It is found that the Her2 levels are significantly reduced by pacOligo$_{10k}$, SNA, and Lipofectamine-complexed DNA. Strikingly, even at a low concentration (10 nM), the pac-DNA10 k was able to reduce Her2 expression to only 5% of untreated, as determined by band densitometry analysis, while scrambled pacOligo$_{10k}$ does not reduce Her2 expression. On the other hand, pacOligo$_{5k}$, $_Y$PEG-DNA, and free DNA show no Her2 expression reduction compared with untreated cells. (FIG. 13) These data demonstrate that DNA stability plays an important role in non-cationic gene regulation; only oligonucleotides with sufficient stability are able to withstand the digestive endosomal processing and perform downstream action. Unprotected nucleic acids are likely cleaved and deactivated by the cells. Because pacOligo consists of non-toxic components (e.g., PEG and DNA), its cytotoxicity is at a minimum. Indeed, MTT cytotoxicity assays for SKOV3 and 4T1 cells show essentially no cytotoxicity at 4000 ng of DNA, the highest concentration tested (FIG. 11 and FIG. 12), while Lipofectamine results in significant cell death (>50%) above 400 ng of DNA.

In summary, the data show that efficient cell uptake and enhanced oligonucleotide stability is a successful combination for non-cationic gene regulation; facilitated endosomal release by a membrane-disrupting agent is not required. The pacOligo has desired characteristics to make it an ideal non-cationic oligonucleotide delivery platform, due to the densely arranged side chains of the biocompatible polymer brush. Because of its ability to shield DNA from proteins and bypass serum opsonization, the pacOligo can be applied in vivo for many oligonucleotide-based applications.

Example 6

PacDNA with Different DNA Attachment Points

The extent of steric protection of the oligonucleotide as a function of the oligo's "depth" into the brush backbone was analyzed. A series of DNA oligonucleotides were synthesized and used to generate different pac-Oligos in which the oligonucleotide is attached to the brush polymer backbone at different locations within the oligonucleotide. The probes are of the same length, and dual-labeled at 5' and 3' with Cy3 and Cy5. (See Table 5) The attachment point is via a T base that is located at different positions in the oligonucleotide sequence. As the attachment point moves from 5' to 3', the 5' end of the DNA moves away from the brush core and the 3' moves towards the core. Thus, it is anticipated that the stability for the 5' end will decrease as the 3' end gains steric protection and thus stability (FIG. 14A). For readout, a complementary quencher strand that has dual quenchers at both the 3' and 5' ends is used to hybridize to the pacOligos. (Table 5) Upon nuclease degradation, signals from Cy3 and Cy5 are simultaneously recorded, giving relative stability information of both termini of the oligonucleotide. The use of oligonucleotides of the same length ensures that hybridization occurs in a consistent fashion (no T. differences between strands), and thus achieves highest accuracy and eliminates the need for normalization of the data. Free DNA strands and strands with a single 40 kDa PEG modification are used as controls. The data, which are shown in FIGS. 14 B and C, confirm the predicted results.

TABLE 5

Oligonucleotides sequence used in this study:

| Item | Sequence |
| --- | --- |
| FT1 | 5'-Cy5-GTG GTG GTG GTG GTG GTG G *T-DBCO* G-Fluorescein-3' (SEQ ID NO.: 14) |
| FT2 | 5'-Cy5-GTG GTG GTG GTG GTG G *T-DBCO* G GTG-Fluorescein-3' (SEQ ID NO.: 15) |
| Complementary strand | 5'-Dabcyl-CAC CAC CAC CAC CAC CAC CAC-Dabcyl-3' (SEQ ID NO. 16) |

What is claimed is:

1. A brush polymer-oligonucleotide conjugate comprising a plurality of oligonucleotides covalently linked to the backbone of a non-cationic, biocompatible brush polymer, wherein the plurality of oligonucleotides is double stranded RNAs that are conjugated to the backbone of the brush polymer via a cleavable bond.

2. The brush polymer-oligonucleotide conjugate of claim 1, wherein the non-cationic, biocompatible brush polymer comprises polyethylene glycol (PEG), a polysaccharide or a zwitterion polymer.

3. The brush polymer-oligonucleotide conjugate of claim 2, wherein the non-cationic, biocompatible brush polymer is PEG.

4. The brush polymer-oligonucleotide conjugate of claim 3, wherein the brush polymer backbone comprises 3 to 60 PEG units.

5. The brush polymer-oligonucleotide conjugate of claim 4, wherein the length and density of the side chains of the brush polymer are sufficient to protect the plurality of oligonucleotides via steric hindrance.

6. The brush polymer-oligonucleotide conjugate of claim 1, wherein the plurality of oligonucleotides further comprises oligonucleotides selected from the group consisting of single stranded DNA, double stranded DNA, single stranded RNA and aptamers.

7. The brush polymer-oligonucleotide conjugate of claim 1, wherein the plurality of oligonucleotides further comprises single stranded DNA having a sequence that is complementary to a pre-selected target polynucleic acid.

8. The brush polymer-oligonucleotide conjugate of claim 1, wherein the plurality of oligonucleotides comprises oligonucleotides from 2 to 85 nucleobases in length.

9. The brush polymer-oligonucleotide conjugate of claim 1, wherein each of the plurality of oligonucleotides is independently conjugated to the backbone of the brush polymer at the 5' or 3' end of the oligonucleotide or attached via a thymidine base of the oligonucleotide.

10. The brush polymer-oligonucleotide conjugate of claim 1, wherein the plurality of oligonucleotides comprises oligonucleotides of different lengths and/or different nucleotide sequences.

11. The brush polymer-oligonucleotide conjugate of claim 1, wherein the at least one of the plurality of oligonucleotides comprises a detectable label.

12. A composition comprising the brush polymer-oligonucleotide conjugate of claim 1 and a pharmaceutically acceptable carrier.

13. A brush polymer-oligonucleotide conjugate comprising a plurality of oligonucleotides covalently linked to the backbone of a non-cationic, biocompatible brush polymer, wherein the plurality of oligonucleotides is double stranded RNAs that are conjugated to the backbone of the brush polymer via a cleavable bond and wherein the brush polymer-oligonucleotide conjugate further comprises at least one oligonucleotide covalently attached to the backbone of the brush polymer via a thymidine base of the oligonucleotide.

14. The brush polymer-oligonucleotide conjugate of claim 13, wherein the thymidine base is located at or near the middle of the nucleotide sequence of each of the at least one of the plurality of oligonucleotides.

15. The brush polymer-oligonucleotide conjugate of claim 13, wherein the at least one of the plurality of oligonucleotides is from 30 to 85 nucleotides in length.

16. A method of inhibiting expression of a gene product encoded by a target polynucleotide comprising contacting the target polynucleotide with the brush polymer-oligonucleotide conjugate of claim 1.

17. A method for promoting cellular uptake of an oligonucleotide comprising delivering an oligonucleotide structure to a subject or a biological sample in an effective amount for promoting cellular uptake of the oligonucleotide in the subject or biological sample, wherein the oligonucleotide structure comprises the brush polymer-oligonucleotide conjugate of claim 1.

18. A method of detecting the presence a target polynucleotide in a subject or a tissue sample obtained from a subject comprising contacting the target polynucleotide with the brush polymer-oligonucleotide conjugate of claim 1.

* * * * *

SEQUENCE LISTING

<160> NUMBER OF SEQ ID NOS: 16

<210> SEQ ID NO 1
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-NH2"
<220> FEATURE:
<221> NAME/KEY: source
<223> OTHER INFORMATION: /note="3'-Fluorescein"

<400> SEQUENCE: 1
cccagccctc                                                          10

<210> SEQ ID NO 2
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-NH2"
<220> FEATURE:
<221> NAME/KEY: source
<223> OTHER INFORMATION: /note="3'-Fluorescein"

<400> SEQUENCE: 2
cccagccttc cagct                                                    15

<210> SEQ ID NO 3
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

```
<220> FEATURE:
<221> NAME/KEY: source
<223> OTHER INFORMATION: /note="5'-Dabcyl"
<220> FEATURE:
<221> NAME/KEY: source
<223> OTHER INFORMATION: /note="3'-Fluorescein"

<400> SEQUENCE: 3
gagggctggg                                                                  10

<210> SEQ ID NO 4
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-Dabcyl"

<400> SEQUENCE: 4
agctggaagg ctggg                                                            15

<210> SEQ ID NO 5
<211> LENGTH: 27
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-NH2"
<220> FEATURE:
<221> NAME/KEY: modified_base
<222> LOCATION: (6)..(6)
<223> OTHER INFORMATION: t-Dabcyl

<400> SEQUENCE: 5
tttactaacc tttccgtcgc agctaaa                                               27

<210> SEQ ID NO 6
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-NH2"
<220> FEATURE:
<221> NAME/KEY: source
<223> OTHER INFORMATION: /note="3'-Cy3"

<400> SEQUENCE: 6
cccagccctc                                                                  10

<210> SEQ ID NO 7
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="5'-Cy5.5"

<400> SEQUENCE: 7
cccagccctc                                                                  10

<210> SEQ ID NO 8
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-DBCO"

<400> SEQUENCE: 8
tttctccatg gtgctcac                                                         18

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-DBCO"
<220> FEATURE:
<221> NAME/KEY: source
<223> OTHER INFORMATION: /note="3'-Fluorescein"

<400> SEQUENCE: 9
tttctccatg gtgctcac                                                         18

<210> SEQ ID NO 10
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-Dabcyl"

<400> SEQUENCE: 10
gtgagcacca tggag                                                            15

<210> SEQ ID NO 11
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-DBCO"
<220> FEATURE:
<221> NAME/KEY: source
<223> OTHER INFORMATION: /note="3'-Cy3"
```

<400> SEQUENCE: 11
tttctccatg gtgctcac                                                                          18

<210> SEQ ID NO 12
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-DBCO"

<400> SEQUENCE: 12
ttttaactct gacatgatgt c                                                                      21

<210> SEQ ID NO 13
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="3'-SH"

<400> SEQUENCE: 13
ctccatggtg ctcactttt ttttt                                                                   25

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-Cy5"
<220> FEATURE:
<221> NAME/KEY: modified_base
<222> LOCATION: (20)..(20)
<223> OTHER INFORMATION: t-DBCO
<220> FEATURE:
<221> NAME/KEY: source
<223> OTHER INFORMATION: /note="3'-Fluorescein"

<400> SEQUENCE: 14
gtggtggtgg tggtggtggt g                                                                      21

<210> SEQ ID NO 15
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-Cy5"
<220> FEATURE:
<221> NAME/KEY: modified_base
<222> LOCATION: (17)..(17)
<223> OTHER INFORMATION: t-DBCO

```
<220> FEATURE:
<221> NAME/KEY: source
<223> OTHER INFORMATION: /note="3'-Fluorescein"

<400> SEQUENCE: 15
gtggtggtgg tggtggtggt g                                              21

<210> SEQ ID NO 16
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="5'-Dabcyl"
<220> FEATURE:
<221> NAME/KEY: source
<223> OTHER INFORMATION: /note="3'-Dabcyl"

<400> SEQUENCE: 16
caccaccacc accaccacca c                                              21
```